(12) United States Patent
Birla

(10) Patent No.: US 10,106,776 B2
(45) Date of Patent: *Oct. 23, 2018

(54) ENERGETIC THREE-DIMENSIONAL ARTIFICIAL CARDIAC PATCH AND USES THEREOF

(71) Applicant: University of Houston, Houston, TX (US)

(72) Inventor: Ravi K. Birla, Sugar Land, TX (US)

(73) Assignee: UNIVERSITY OF HOUSTON, Houston, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/270,766

(22) Filed: May 6, 2014

(65) Prior Publication Data

US 2014/0328806 A1 Nov. 6, 2014

Related U.S. Application Data

(60) Provisional application No. 61/819,843, filed on May 6, 2013.

(51) Int. Cl.
| | |
|---|---|
| *C12N 5/077* | (2010.01) |
| *A61K 35/34* | (2015.01) |
| *A61L 27/38* | (2006.01) |
| *A61L 27/22* | (2006.01) |
| *A61L 27/34* | (2006.01) |
| *A61L 27/52* | (2006.01) |
| *A61K 38/18* | (2006.01) |

(52) U.S. Cl.
CPC ............ *C12N 5/0657* (2013.01); *A61K 35/34* (2013.01); *A61K 38/18* (2013.01); *A61L 27/225* (2013.01); *A61L 27/34* (2013.01); *A61L 27/3826* (2013.01); *A61L 27/52* (2013.01); *A61L 2430/20* (2013.01); *C12N 2533/30* (2013.01); *C12N 2533/56* (2013.01)

(58) Field of Classification Search
CPC .. A61L 27/34; A61L 2430/20; A61L 2430/40; A61L 27/225; A61L 27/3604; A61L 27/3826; A61L 27/3834; A61F 2/08; A61F 2002/0894; A61M 1/12; A61M 1/122; C08L 83/04; C12N 2533/56; C12N 5/0657; C12N 2533/90; C12N 2501/734

See application file for complete search history.

(56) References Cited

U.S. PATENT DOCUMENTS

| | | | | |
|---|---|---|---|---|
| 6,787,357 | B2 * | 9/2004 | Bowlin | ............. A61L 15/32 435/325 |
| 2004/0132184 | A1 * | 7/2004 | Dennis | ............. C12N 5/0658 424/423 |
| 2008/0119385 | A1 * | 5/2008 | Michal | ............. A61K 35/28 424/93.7 |
| 2015/0125952 | A1 * | 5/2015 | Kim | ............. A61L 27/14 435/366 |

OTHER PUBLICATIONS

Amir et al. (2008) Annals of Thoracic Surgery 86(4): 1311-9.*
Chiu LL, Iyer RK, Reis LA, Nunes SS, Radisic M. Cardiac tissue engineering: current state and perspectives. Front Biosci. 2012;17:1533-50.
Curtis MW, Russell B. Cardiac tissue engineering. J.Cardiovasc. Nurs. Mar. 2009;24(2):87-92. PMCID:PMC2700236.
Hecker L, Birla RK. Engineering the heart piece by piece: state of the art in cardiac tissue engineering. Regen.Med. Mar. 2007;2(2):125-44.
Baar K, Birla R, Boluyt MO, Borschel GH, Arruda EM, Dennis RG. Self-organization of rat cardiac cells into contractile 3-D cardiac tissue. FASEB Journal. 2005;(2):275-7.
Huang YC, Khait L, Birla RK. Contractile three-dimensional bioengineered heart muscle for myocardial regeneration. J.Biomed. Mater.Res.A Mar. 1, 2007;80(3):719-31.
Blan NR, Birla RK. Design and fabrication of heart muscle using scaffold-based tissue engineering. Journal of Biomedical Materials Research Jul. 2008;Part(1):195-208.
Galvez-Monton C, Prat-Vidal C, Roura S, Soler-Botija C, Bayes-Genis A. Cardiac Tissue Engineering and the Bioartificial Heart. Rev.Esp.Cardiol. May 2013;66(5):391-9.
Eschenhagen T, Fink C, Remmers U, Scholz H, Wattchow J, Weil J, Zimmermann W, Dohmen HH, Schafer H, Bishopric N, et al. Three-dimensional reconstitution of embryonic cardiomyocytes in a collagen matrix: a new heart muscle model system. FASEB Journal. Jul. 1997;11(8):683-94.

(Continued)

*Primary Examiner* — Lisa J Hobbs
(74) *Attorney, Agent, or Firm* — Winstead PC

(57) ABSTRACT

In some embodiments, the present disclosure provides a method for fabricating a three-dimensional artificial cardiac patch construct. In some embodiments, such method includes the steps of coating a substrate with an organic polymer; allowing the organic polymer coating to air dry; mounting anchors on the organic polymer coating; and sterilizing the organic polymer coating and the anchors. In further embodiments, the method includes the steps of forming a biodegradable gel-based support scaffold on top of the organic polymer coating and seeding the biodegradable gel-based support scaffold with neonatal cardiac cells. In yet further embodiments, the method comprises culturing the neonatal cardiac cells in vitro to form a real cardiac layer, under culture conditions that are suitable for the cells to self-organize into a monolayer and detach from the substrate to form the three-dimensional cardiac patch. In some embodiments, the present disclosure pertains to a method of treatment of cardiac tissue injury in a subject in need thereof. In some embodiments, the method includes implanting the three-dimensional artificial cardiac patch described above in the injured area of the subject. In another embodiment the present disclosure provides a composition comprising the three-dimensional artificial cardiac patch described above. Additional embodiments of the present disclosure pertain to a medicament including the three-dimensional artificial cardiac patch described above.

26 Claims, 9 Drawing Sheets

(56) References Cited

OTHER PUBLICATIONS

Akins RE, Boyce RA, Madonna ML, Schroedl NA, Gonda SR, McLaughlin TA, Hartzell CR. Cardiac organogenesis in vitro: reestablishment of three-dimensional tissue architecture by dissociated neonatal rat ventricular cells. Tissue Engineering Apr. 1999;5(2):103-18.

Carrier RL, Papadaki M, Rupnick M, Schoen FJ, Bursac N, Langer R, Freed LE, Vunjak-Novakovic G. Cardiac tissue engineering: cell seeding, cultivation parameters, and tissue construct characterization. Biotechnology & Bioengineering Sep. 5, 1999;64(5):580-9.

Bursac N, Papadaki M, Cohen RJ, Schoen FJ, Eisenberg SR, Carrier R, Vunjak-Novakovic G, Freed LE. Cardiac muscle tissue engineering: toward an in vitro model for electrophysiological studies. American Journal of Physiology Aug. 1999;277(2:Pt 2):t-44.

Li RK, Jia ZQ, Weisel RD, Mickle DA, Choi A, Yau TM. Survival and function of bioengineered cardiac grafts. Circulation Nov. 9, 1999;100(19:Suppl):Suppl-9.

Zimmermann WH, Fink C, Kralisch D, Remmers U, Weil J, Eschenhagen T. Three-dimensional engineered heart tissue from neonatal rat cardiac myocytes. Biotechnology & Bioengineering. Apr. 5, 2000;68(1):106-14.

Leor J, Aboulafia-Etzion S, Dar A, Shapiro L, Barbash IM, Battler A, Granot Y, Cohen S. Bioengineered cardiac grafts: A new approach to repair the infarcted myocardium? Circulation Nov. 7, 2000;102(19:Suppl 3):Suppl-61.

Li RK, Yau TM, Weisel RD, Mickle DA, Sakai T, Choi A, Jia ZQ. Construction of a bioengineered cardiac graft. Journal of Thoracic & Cardiovascular Surgery Feb. 2000;119(2):368-75.

Papadaki M, Bursac N, Langer R, Merok J, Vunjak-Novakovic G, Freed LE. Tissue engineering of functional cardiac muscle: molecular, structural, and electrophysiological studies. American Journal of Physiology—Heart & Circulatory Physiology Jan. 2001;280(1):H168-H178.

Shimizu T, Yamato M, Kikuchi A, Okano T. Two-dimensional manipulation of cardiac myocyte sheets utilizing temperature-responsive culture dishes augments the pulsatile amplitude. Tissue Engineering Apr. 2001;7(2):141-51.

Shimizu T, Yamato M, Akutsu T, Shibata T, Isoi Y, Kikuchi A, Umezu M, Okano T. Electrically communicating three-dimensional cardiac tissue mimic fabricated by layered cultured cardiomyocyte sheets. Journal of Biomedical Materials Research 2002;60(1):110-7.

Shimizu T, Yamato M, Isoi Y, Akutsu T, Setomaru T, Abe K, Kikuchi A, Umezu M, Okano T. Fabrication of pulsatile cardiac tissue grafts using a novel 3-dimensional cell sheet manipulation technique and temperature-responsive cell culture surfaces. Circulation Research Feb. 22, 2002;90(3):e40.

Dar A, Shachar M, Leor J, Cohen S. Optimization of cardiac cell seeding and distribution in 3D porous alginate scaffolds. Biotechnology & Bioengineering. Nov. 5, 2002;80(3):305-12.

Wei HJ, Chen SC, Chang Y, Hwang SM, Lin WW, Lai PH, Chiang HK, Hsu LF, Yang HH, Sung HW. Porous acellular bovine pericardia seeded with mesenchymal stem cells as a patch to repair a myocardial defect in a syngeneic rat model. Biomaterials Nov. 2006;27(31):5409-19.

Wei HJ, Chen CH, Lee WY, Chiu I, Hwang SM, Lin WW, Huang CC, Yeh YC, Chang Y, Sung HW. Bioengineered cardiac patch constructed from multilayered mesenchymal stem cells for myocardial repair. Biomaterials Sep. 2008;29(26):3547-56.

Prabhakaran MP, Kai D, Ghasemi-Mobarakeh L, Ramakrishna S. Electrospun biocomposite nanofibrous patch for cardiac tissue engineering. Biomed.Mater. Oct. 2011;6(5):055001.

Yuan YK, Sullivan KE, Black LD. Encapsulation of cardiomyocytes in a fibrin hydrogel for cardiac tissue engineering. J.Vis.Exp. 2011;(55). PMCID:PMC3230174.

Prabhakaran MP, Nair AS, Kai D, Ramakrishna S. Electrospun composite scaffolds containing poly(octanediol-co-citrate) for cardiac tissue engineering. Biopolymers Jul. 2012;97(7):529-38.

Ravichandran R, Venugopal JR, Sundarrajan S, Mukherjee S, Sridhar R, Ramakrishna S. Expression of cardiac proteins in neonatal cardiomyocytes on PGS/fibrinogen core/shell substrate for Cardiac tissue engineering. Int.J.Cardiol. May 5, 2012.

Fleischer S, Feiner R, Shapira A, Ji J, Sui X, Daniel WH, Dvir T. Spring-like fibers for cardiac tissue engineering. Biomaterials Nov. 2013;34(34):8599-606.

Reddy CS, Venugopal JR, Ramakrishna S, Zussman E. Polycaprolactone/oligomer compound scaffolds for cardiac tissue engineering. J.Biomed.Mater.Res.A Oct. 2014;102(10):3713-25.

Annabi N, Tsang K, Mithieux SM, Nikkhah M, Ameri A, Khademhosseini A, Weiss AS. Highly Elastic Micropatterned Hydrogel for Engineering Functional Cardiac Tissue. Adv.Funct.Mater. Oct. 18, 2013;23(39). PMCID:PMC3850066.

Matsuura K, Masuda S, Shimizu T. Cell sheet-based cardiac tissue engineering. Anat.Rec.(Hoboken.) Jan. 2014;297(1):65-72.

Yu J, Lee AR, Lin WH, Lin CW, Wu YK, Tsai WB. Electrospun PLGA fibers incorporated with functionalized biomolecules for cardiac tissue engineering. Tissue Eng Part A Jul. 2014;20(13-14):1896-907. PMCID:PMC4086675.

Qazi TH, Rai R, Dippold D, Roether JE, Schubert DW, Rosellini E, Barbani N, Boccaccini AR. Development and characterization of novel electrically conductive PANI-PGS composites for cardiac tissue engineering applications. Acta Biomater. Jun. 2014;10(6):2434-45.

Cui H, Liu Y, Cheng Y, Zhang Z, Zhang P, Chen X, Wei Y. In vitro study of electroactive tetraaniline-containing thermosensitive hydrogels for cardiac tissue engineering. Biomacromolecules. Apr. 14, 2014;15(4):1115-23.

Ehler E, Jayasinghe SN. Cell electrospinning cardiac patches for tissue engineering the heart. Analyst Sep. 21, 2014;139(18):4449-52.

Dhingra S, Weisel RD, Li RK. Synthesis of aliphatic polyester hydrogel for cardiac tissue engineering. Methods Mol.Biol. 2014;1181:51-9.

Shevach M, Fleischer S, Shapira A, Dvir T. Gold nanoparticle-decellularized matrix hybrids for cardiac tissue engineering. Nano. Lett. Oct. 8, 2014;14(10):5792-6.

Baheiraei N, Yeganeh H, Ai J, Gharibi R, Azami M, Faghihi F. Synthesis, characterization and antioxidant activity of a novel electroactive and biodegradable polyurethane for cardiac tissue engineering application. Mater.Sci.Eng C Mater.Biol.Appl. Nov. 1, 2014;44:24-37.

Bhaarathy V, Venugopal J, Gandhimathi C, Ponpandian N, Mangalaraj D, Ramakrishna S. Biologically improved nanofibrous scaffolds for cardiac tissue engineering. Mater.Sci.Eng C Mater.Biol.Appl. Nov. 1, 2014;44:268-77.

Tallawi M, Zebrowski D, Rai R, Roether J, Schubert D, El FM, Engel F, Aifantis K, Boccaccini AR. Poly(glycerol sebacate)/poly(butylene succinate-dilinoleate) (PGS/PBS-DLA) fibrous scaffolds for cardiac tissue engineering. Tissue Eng Part C Methods Dec. 1, 2014.

Williams C, Budina E, Stoppel WL, Sullivan KE, Emani S, Emani SM, Black LD, III. Cardiac Extracellular Matrix-Fibrin Hybrid Scaffolds with Tunable Properties for Cardiovascular Tissue Engineering. Acta Biomater. Nov. 25, 2014.

* cited by examiner

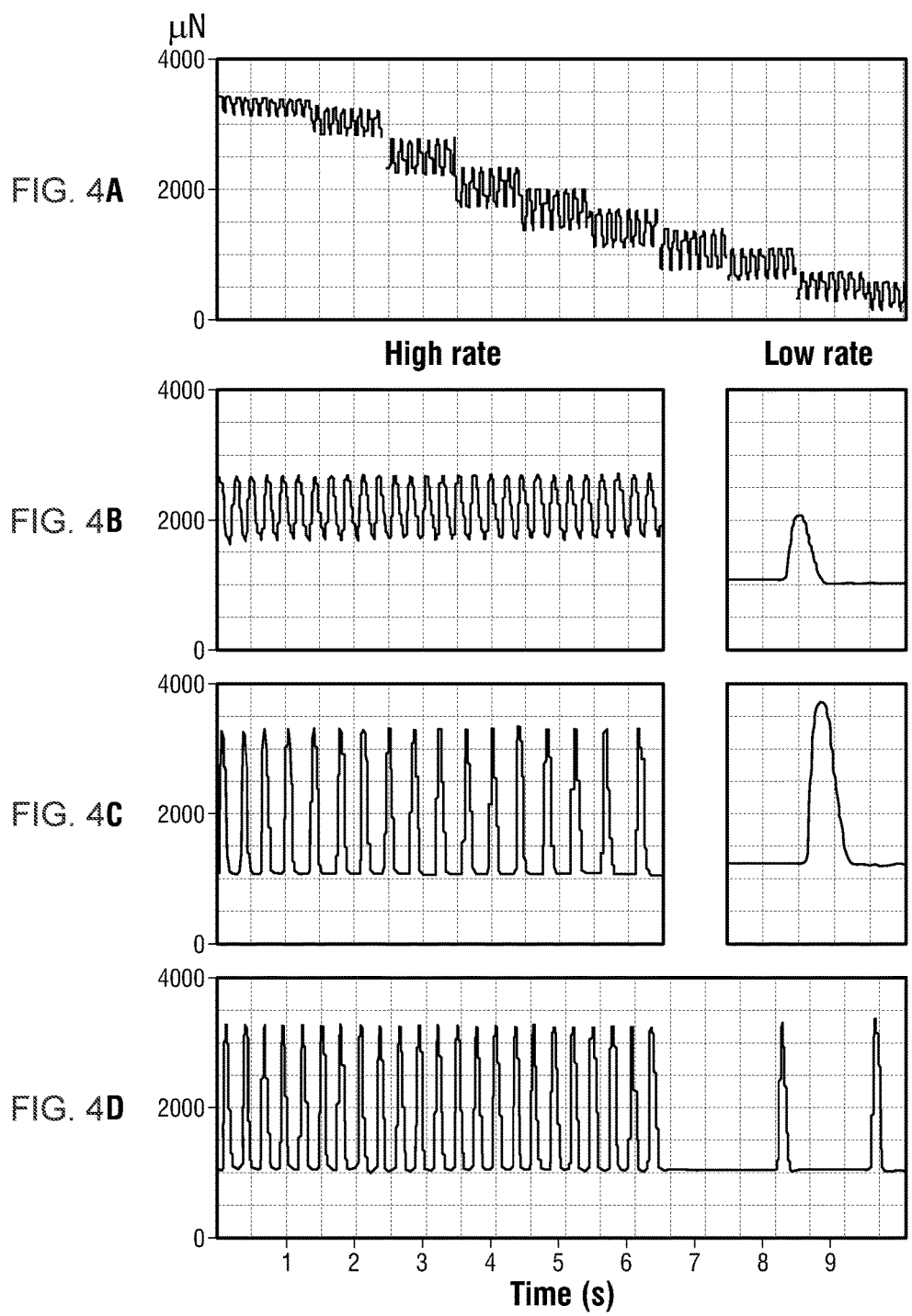

ENERGETIC THREE-DIMENSIONAL ARTIFICIAL CARDIAC PATCH AND USES THEREOF

CROSS REFERENCE TO RELATED APPLICATIONS

This application claims priority to U.S. Provisional Patent Application No. 61/819,843, filed on May 6, 2013. The entirety of the aforementioned application is incorporated herein by reference.

STATEMENT REGARDING FEDERALLY-SPONSORED RESEARCH

This invention was made, at least in part, with U.S. government support under grant No. RO1-EB011516 awarded by the National Institute of Health. The U.S. government may have certain rights in this invention.

BACKGROUND

Heart transplantation has been the most successful modality in the treatment of severe Chronic Heart Failure. However, widespread applicability is limited by the chronic shortage of donor organs. Engineered cardiac tissues, which embed enough cells and provide additional tension support, possess a tremendous potential in treating large injured areas of the heart and in replacing congenital defects of the heart. So far, prior art methods for reconstruction of a functional heart tissue have been fraught with problems. In particular, problems with vascularization of the construct still limit the use of conventional tissue scaffolds in the replacement of large-sized tissue defects. Additionally, reproducing the special organizational, mechanical and elastic properties of native myocardium represents a significant challenge from the perspective of tissue engineering scaffolds. Thus, there exists a need to have engineered cardiac tissues that display functional and morphological properties of native myocardium and remain viable after implantation.

SUMMARY

In some embodiments, the present disclosure provides a method for fabricating a three-dimensional artificial cardiac patch construct. In some embodiments, such method includes the steps of coating a substrate with an organic polymer; allowing the organic polymer coating to air dry; mounting anchors on the organic polymer coating; and sterilizing the organic polymer coating. In further embodiments, the method includes forming a biodegradable gel-based support scaffold on top of the organic polymer coating; and seeding the biological support scaffold with neonatal cardiac cells. In yet further embodiments; the method comprises culturing the neonatal cardiac cells in vitro to form a real cardiac layer, under culture conditions that are suitable for the cells to self-organize into a monolayer and detach from the substrate to form the three-dimensional cardiac patch construct.

In some embodiments, the present disclosure pertains to a method of treatment of cardiac tissue injury in a subject in need thereof. In some embodiments, the method includes implanting the aforementioned three-dimensional artificial cardiac patch in the injured area of the subject.

In yet another embodiment, the present disclosure provides a three-dimensional artificial cardiac patch comprising an organic polymer coated on a substrate; a biodegradable gel-based support scaffold formed on top of the organic polymer; and cardiac cells, wherein the cardiac cells are seeded on the biodegradable gel-based scaffold. In an embodiment, the three-dimensional artificial cardiac patch further comprises at least one agent from the group consisting of survival factors, growth factors, pharmacological agents, angiogenic factors, beta-blockers or ACE inhibitors.

Additional embodiments of the present disclosure pertain to a medicament comprising the aforementioned composition. In some embodiments the medicament further comprises at least one agent from the group consisting of survival factors, growth factors, pharmacological agents, angiogenic factors, beta-blockers or ACE inhibitors.

The above objects and other objects, features, and advantages of the present invention are readily apparent from the following detailed description of the best mode for carrying out the invention when taken in conjunction with the accompanying drawings.

BRIEF DESCRIPTION OF THE FIGURES

In order that the manner in which the above recited and other advantages and objects of the invention are obtained, a more particular description of the invention briefly described above will be rendered by reference to specific embodiments thereof, which are illustrated in the appended Figures. Understanding that these Figures depict only typical embodiments of the invention and are therefore not to be considered limiting of its scope, the invention will be described with additional specificity and detail through the use of the accompanying Figures in which:

FIGS. 4A-4G depict the relationship between the density of the cells initially seeded in the biodegradable gel-based support scaffold and contractile force. FIG. 4A is a representative graph depicting the steady contraction of the patches fabricated with cell densities ranging from 1M to 3M; representative sample of high and low rate contractile force from 2M (FIG. 4B), 4M (FIG. 4C), and 6M (FIG. 4D) patches; FIG. 4E, is a graph of representative average contractile forces from 1M to 3M patches at various pretensions; Graphs of average contractile force for cell densities of 1M, 2M, 3M, 4M, 5M and 6M loaded with a pretension range of 1000 to 2000 μN from high rate (FIG. 4F), and low rate (FIG. 4G) contractions.

FIGS. 5A-5C illustrate the representative of the continual and singular contractile forces for cell densities 2M (FIG. 5A), 4M (FIG. 5B) and 6M (FIG. 5C). FIG. 5D represents the graph for average contractile forces from continual contractions. FIG. 5E shows the graph for average contractile forces from singular contraction for cell densities 1M, 2M, 3M, 4M, 5M, and 6M.

FIG. 6A (100×) cross-section, FIG. 6B (100×), and FIG. 6C (400×) planar sections directly from frozen samples illustrate the composition of the sample patch obtained with light microscope; Arrow heads (FIG. 6A) indicate the real cardiac layer. FIG. 6D (200×) cross-section, FIG. 6E (200×) and FIG. 6F (400×) image from Masson trichrome; Arrow heads in FIG. 6D indicate the real cardiac layer, and arrows in FIG. 6E is the fibrin gel network underneath the real cardiac layer; FIG. 6G is a planar image showing growth of heart muscle (α-Actinin), endothelial cells (vWF) and nuclear division (Ki67), the arrows indicate a nucleus in karyokinesis (FIG. 6H); FIG. 6I is a planar image showing gap junction protein (Connexin 43) and endothelial cells (vWF) in the cultured tissue. FIGS. 7A-7Q illustrate the real cardiac layer thickness and gap junctions in the patch. FIGS. 7A-7C are cross-sections showing real cardiac layer thickness and the support scaffold fibrin network in the patch by Masson's trichrome staining for cell densities of 2M (FIG. 7A), 4M (FIG. 7B), and 6M (FIG. 7C), respectively; FIGS. 7D-7F are cross-sections showing growth of heart muscles (α-Actinin) and gap junctions (Cx43) for 2M ((FIG. 7D), 4M (FIG. 7E) and 6M (FIG. 7F) patches, respectively; FIGS. 7G, 7J and 7M show the total signal volumes, FIGS. 7H, 7K and 7N show the signal volumes of Cx43, and 7I, 7K and 7O show the signal volumes of (α-Actinin for 2M, 4M and 6M patches, respectively; FIG. 7P is a graph showing differences in patch thickness; and FIG. 7Q depicts the signal volume indexes of Cx43 for 2M, 4M and 6M patches.

DETAILED DESCRIPTION

Figure 1:
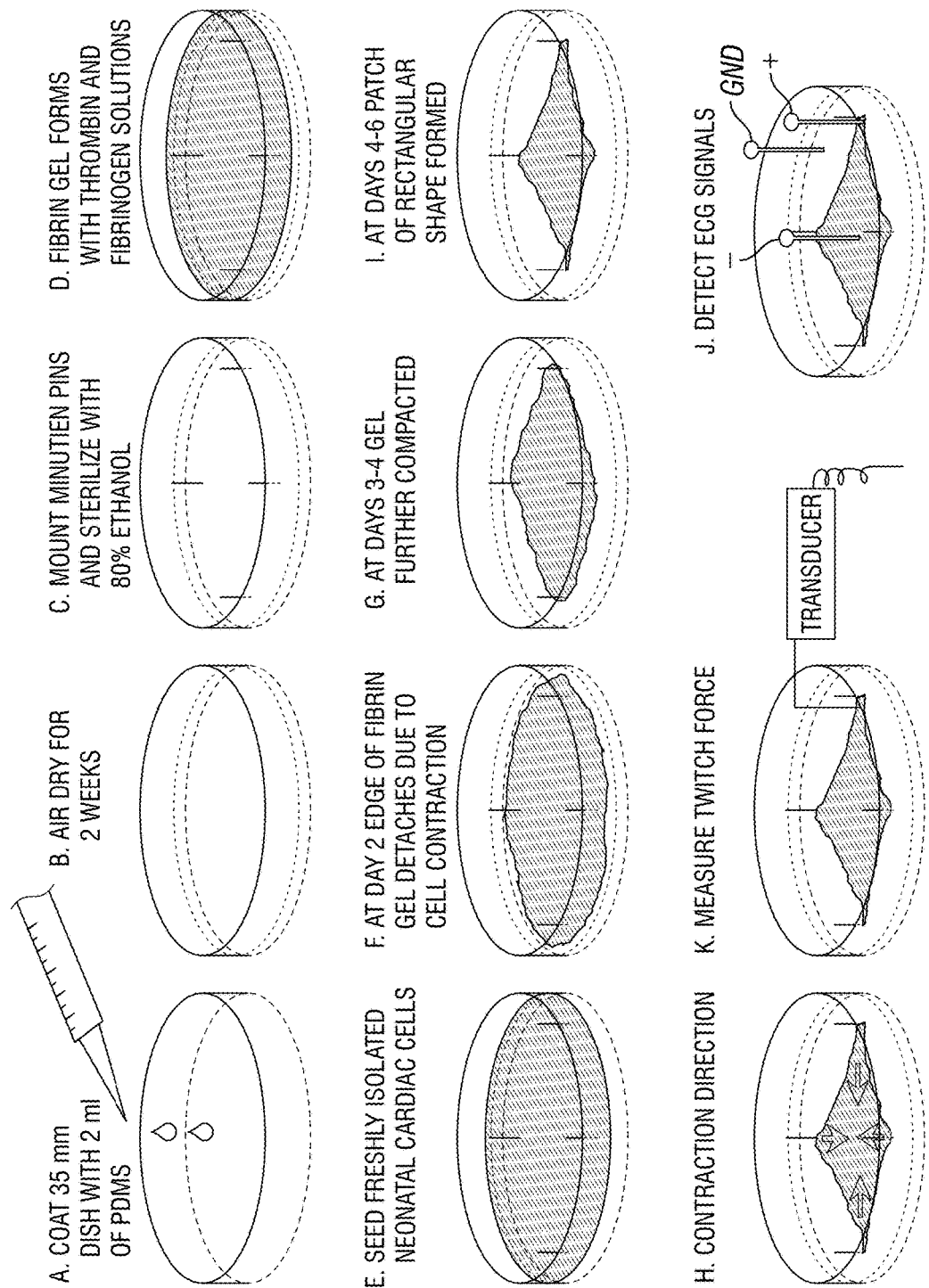
FIGS. 1A-1K depict the schematics of methods for fabrication of the three-dimensional artificial cardiac patch construct.

It is to be understood that both the foregoing general description and the following detailed description are exemplary and explanatory only, and are not restrictive of the invention, as claimed. In this application, the use of the singular includes the plural, the word "a" or "an" means "at least one", and the use of "or" means "and/or", unless specifically stated otherwise. Furthermore, the use of the term "including", as well as other forms, such as "includes" and "included", is not limiting. Also, terms such as "element" or "component" encompass both elements or components comprising one unit and elements or components that comprise more than one unit unless specifically stated otherwise. Parameters disclosed herein (e.g., temperature, time, concentration, etc.) may be approximate.

The section headings used herein are for organizational purposes only and are not to be construed as limiting the subject matter described. All documents, or portions of documents, cited in this application, including, but not limited to, patents, patent applications, articles, books, and treatises, are hereby expressly incorporated herein by reference in their entirety for any purpose. In the event that one or more of the incorporated literature and similar materials defines a term in a manner that contradicts the definition of that term in this application, this application controls.

"Angiogenesis" as used herein, generally refers to the growth of blood vessels in the three-dimensional artificial cardiac patch construct. The angiogenesis may occur in response to a stimulus, for instance, in response to administration of an effective amount of an angiogenic factor.

The term "angiogenic factor" as used herein shall be given its ordinary meaning and shall refer to a molecule capable of activating or otherwise promoting angiogenesis.

The term "cardiac patch" as used herein shall be given its ordinary meaning and shall refer to tissue of the heart, for example, the epicardium, myocardium or endocardium, or portion thereof, of the heart.

The term "cardiac tissue injury" as used herein shall be given its ordinary meaning and shall refer to a cardiac tissue that is, for example, ischemic, infarcted, reperfused, or otherwise focally or diffusely injured or diseased. Injuries associated with a cardiac tissue include any areas of abnormal tissue in the heart, including any areas of abnormal tissue caused by a disease, disorder or injury and includes damage to the epicardium, endocardium and/or myocardium. Non-limiting examples of causes of cardiac tissue injuries include acute or chronic stress (e.g., systemic hypertension, pulmonary hypertension or valve dysfunction), atheromatous disorders of blood vessels (e.g., coronary artery disease), ischemia, infarction, inflammatory disease and cardiomyopathies, myocarditis or congestive heart failure.

The term "Animal", or "Mammal," as used herein, includes animals and humans. Thus, when referring to processes such as harvesting tissue from an animal, it is intended that the animal can be a human. Although at times reference may be made herein to "an animal or human," this is not intended to imply that the term "animal" does not include a human.

Additionally, the term as Subject" or "Recipient," as used herein, includes individuals who require intervention or manipulation due to a disease state, treatment regimen or experimental design.

"Biocompatible," as used herein, generally refers to an autologous cell or tissue that originates or is derived from the subject or recipient.

The phrases "conditions suitable for cells to self-organize" or "appropriate cell culture conditions" for a suitable cell type, as used herein, generally refers to an environment with conditions of temperature, pressure, humidity, nutrient and waste exchange, and gas exchange that are permissive for the survival and reproduction of the cells. With respect to any particular type of cell, an environment suitable for growth may require the presence of particular nutrients or growth factors needed or conducive to the survival and/or reproduction of the cells.

"Engineered cardiac tissue construct" or "cardiac patch", or "artificial cardiac patch construct" as used herein, generally refers to three dimensional mass of living mammalian tissue produced primarily by growth in vitro on a substrate. The construct may include one or more types of cells or tissues. For example, the construct may be made up of myocytes cultured in conjunction with other cell types, such as endocardial cells, vascular smooth muscle cells, vascular endothelium, fibroblast, and adrenergic cells, or various subsets of those cell types. The term also encompasses a three-dimensional mass of living mammalian tissue produced at least in part by growth in vivo on a substrate. More particularly, constructs may include two or three-dimensional tissue which share critical structural and functional characteristics with intact cardiac tissue, such as distinctive multicellular organization and oriented contractile function.

"Real Cardiac Layer," as used herein, generally refers to a self-organized monolayer of the neonatal cardiac cells and naturally produced extracellular matrix on top of the biological support scaffold.

As used herein, the terms "treat," "treatment" and "treating" shall be given their ordinary meaning and shall refer to the reduction or amelioration of the progression, severity, and/or duration of a cardiac tissue injury or a symptom thereof. Treatment as used herein includes, but are not limited to, preserving the injured cardiac tissue, regenerating new cardiac tissue, increasing blood flow to the injured tissue, increasing myocardial perfusion, improving global cardiac function (e.g., stroke volume, ejection fraction, and cardiac output) and regional cardiac function (e.g., ventricular wall thickening, segmental shortening and heart pumping).

Tissue engineering combines cellular and molecular biology with material and mechanical sciences to provide an alternative to organ and tissue transplants, which face a limited supply of donor organs. Engineered cardiac tissues, constructed with isolated cells on a natural or synthetic scaffold, have tremendous potential to offer alternative treatment modalities in the healing process of large injured areas and in repairing congenital defects of the heart. By embedding a sufficient number of cells in the tissue and by providing additional tension support to the damaged area, engineered cardiac tissues may circumvent low rates of cell engraftment observed with intracoronary delivery and poor cell survival with intramyocardial injection.

Several criteria for engineered cardiac tissue constructs or cardiac patches have been proposed. These constructs should display functional and morphological properties similar to native heart muscle and remain viable after implantation. The spontaneous contraction twitch forces, generated without any treatment, by seeding neonatal rat heart cells on fibrin gel, exhibit a novel natural instinct. The engineered cardiac tissue constructs of the present disclosure, not only exhibit endothelial cell growth and robust cellular division, but also demonstrate electromechanical coupling protein expression, which can sustain native electrical propagation. Furthermore, in some embodiments of the present disclosure, it is possible to use host origin fibrinogen and thrombin to produce nonimmunogenic fibrin scaffolds before in vivo application.

Neonatal cardiomyocytes possess a tremendous differentiation potential and regenerative capacity. For example, the hearts of 1-day-old neonatal mice can regenerate after a partial surgical resection. Previous methods have utilized cardiomyocytes from 1-3 day old neonatal rats, embedded in collagen type I supplemented with Matrigel, to fabricate a 3D heart tissue. Under optimal supplementation, for instance culturing under auxotonic load or with insulin, such constructs demonstrate a maximal twitch tension of up to 2600±100 μN. A model for the self-organization of primary cardiac cells on laminin substrate to form functional 3D heart muscle, termed cardioids, which exhibited several physiological performance metrics comparable to normal mammalian cardiac tissue and generated twitch forces of 200-300 μN by electrically pacing at frequencies of 1-10 Hz without any signs of fatigue, is disclosed in U.S. Patent Application No. US 2004/0132184, which is incorporated herein by reference in its entirety.

However, the use of these conventional tissue scaffolds is limited by lack of adequate vascularization of such constructs as well as the challenge of reproducing the special organizational, mechanical and elastic properties of native myocardium. The present disclosure addresses these needs. In addition, in some embodiments of the present disclosure, the scaffold is fabricated using a porous fibrin gel, which supports nutrient to the cells in order to maintain cell viability and tissue functionality.

Fibrin is a natural, self-assembling peptide found in the body that is used to form clots along damaged endothelium. Fibrin possesses many interesting properties, such as biocompatibility, bioresorbability, ease of processing, ability to tailor conditions of polymerization, and potential for incorporation of both cells and cell mediators. Thrombin and fibrinogen, which react to form fibrin gel, can be produced from the patient's own blood, thus reducing the potential risk of foreign body reaction or infection when used as component in clinical application. Native, fully-hydrated fibrin gels form at different fibrinogen and thrombin concentrations and at different ionic strengths. Fibrin alone, or in combination with other materials, has been used as a biological scaffold for stem and primary cells to regenerate adipose tissue, bone, cardiac tissue, cartilage, liver, nervous tissue, ocular tissue, skin, tendons, and ligaments.

In some embodiments of the present disclosure, the fibrin support scaffold was developed with human fibrinogen and thrombin and the cardiac cells were well incorporated into the fibrin network. In some embodiments, a thin layer of real cardiac tissue (FIGS. 6A, 6D) was seen on the top of fibrin gel network. In some embodiments, the thickness of the real cardiac tissue layer varied with the plated cell density, with the 4 million cell (4M) and 6 million cell (6M) patches having a significantly thicker layer than the 2 million cell (2M) patches. The reason for this difference might result from the lower cell density and/or the growth rate of each cell type within the patch. Due to overpopulation and the different growth rates for each cell type (fibroblasts, cardiomyocytes, endothelial cells, smooth muscle cells and cardiac stem cells), the cells in the uppermost portion of real cardiac layer of 5 and 6M patches began to die and detach from day 4 (arrow head, FIG. 2) because of the poor nutrients supply underneath. Thus, in some embodiments of the present disclosure, in terms of cell survivability and morphology, the optimal density for constructing the cardiac patch may be 4 million (4M) cells.

Freshly isolated neonatal cardiac cells consist of fibroblasts, cardiomyocytes, smooth muscle cells, endothelial cells and cardiac stem cells. The proliferation rate of cardiac cells is higher in the fetal stage than in the neonatal stage, and greatly diminishes in adulthood. In an exemplary embodiment, 2 to 3-day-old rat cardiac cells were used to construct the cardiac patch. In some embodiments, the cardiac patch of the present disclosure stained positive for vWF, which is secreted by endothelial cells lining a blood vessel, thereby indicating presence of endothelial cells (FIGS. 6G, and 6I). In further embodiments, a positive staining for vWF in the cardiac patch indicated that there were potential angiogenesis buds, which would be suitable to grow and connect to host micro blood vessels and bring nutrients into the cardiac patch during in vivo applications. Further, in some embodiments, a positive staining for ki67 in the cardiac patch indicated that the cardiac patch had ongoing robust cell proliferation (FIGS. 6G, 6H). Ki67 is a nuclear and nucleolar protein which is tightly associated with somatic cell proliferation.

Figure 6:
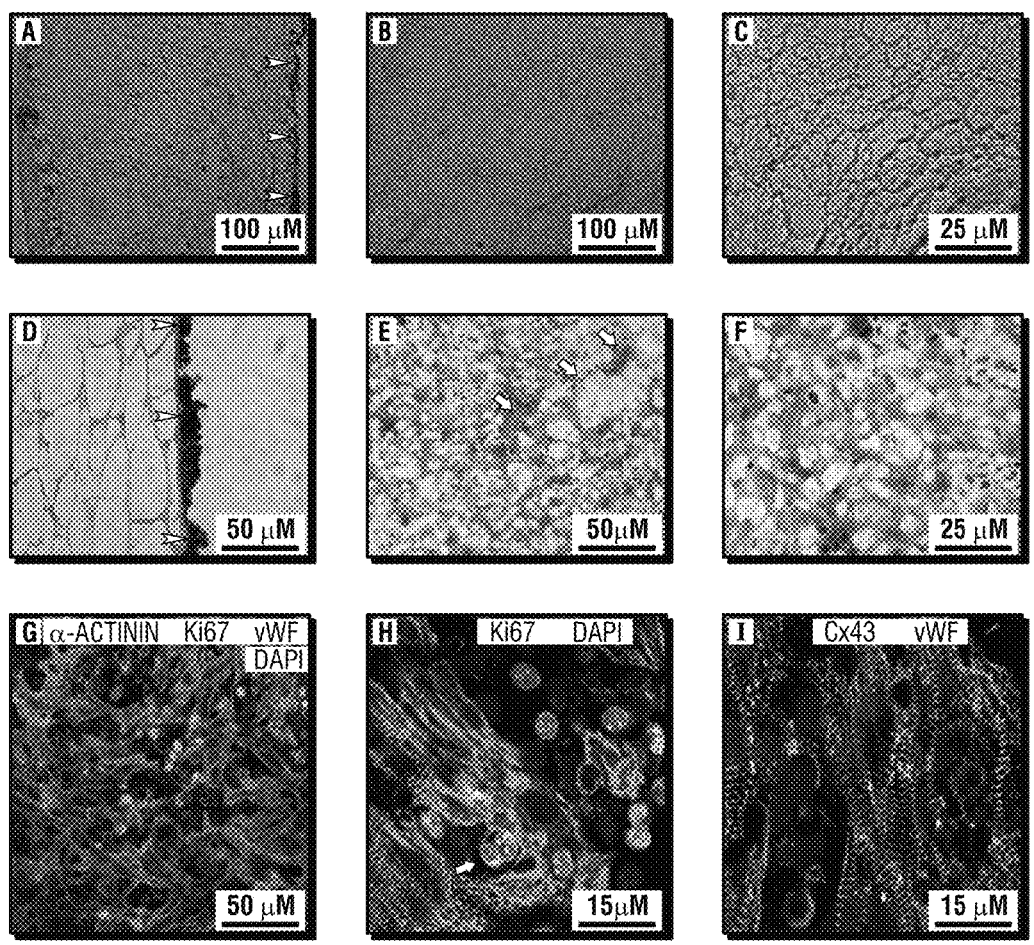
FIGS. 6A-6I show the patch morphology of the three-dimensional artificial cardiac patch at different magnifications.
Figure 7:
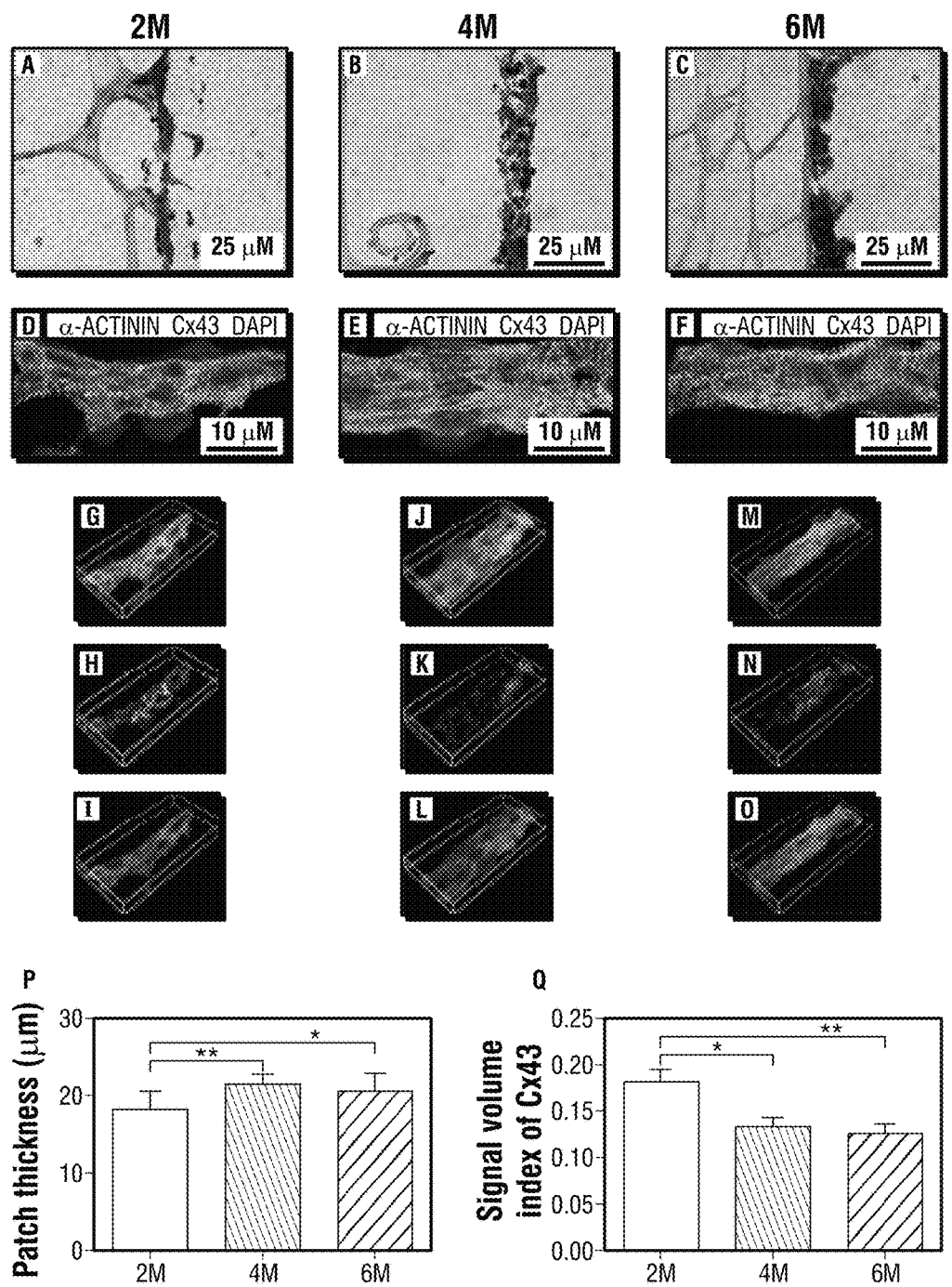

In some embodiments, the cardiac patch of the present disclosure demonstrated positive staining for the Connexin 43 (Cx43) protein, thereby indicating that cardiomyocytes in the present cardiac tissue patch possess electromechanical coupling (FIGS. 6I, 7D, 7F).

In some embodiments of the present disclosure, the cardiac patches can sustain electrical propagation with speeds that would be close to native tissues, as indicated by the detected electrocardiogram (ECG) signal and the natural, adult-heart-like QRS complex. The R wave amplitudes increased with thickness of real cardiac tissue; as shown in FIGS. 5A-5C, FIG. 4E. In a preferred embodiment, cardiac patches formed with 4M and 6M patches exhibit greater R wave amplitude than 2M patch because they possess more cardiomyocytes, which can generate a higher depolarization current.

Figure 3:
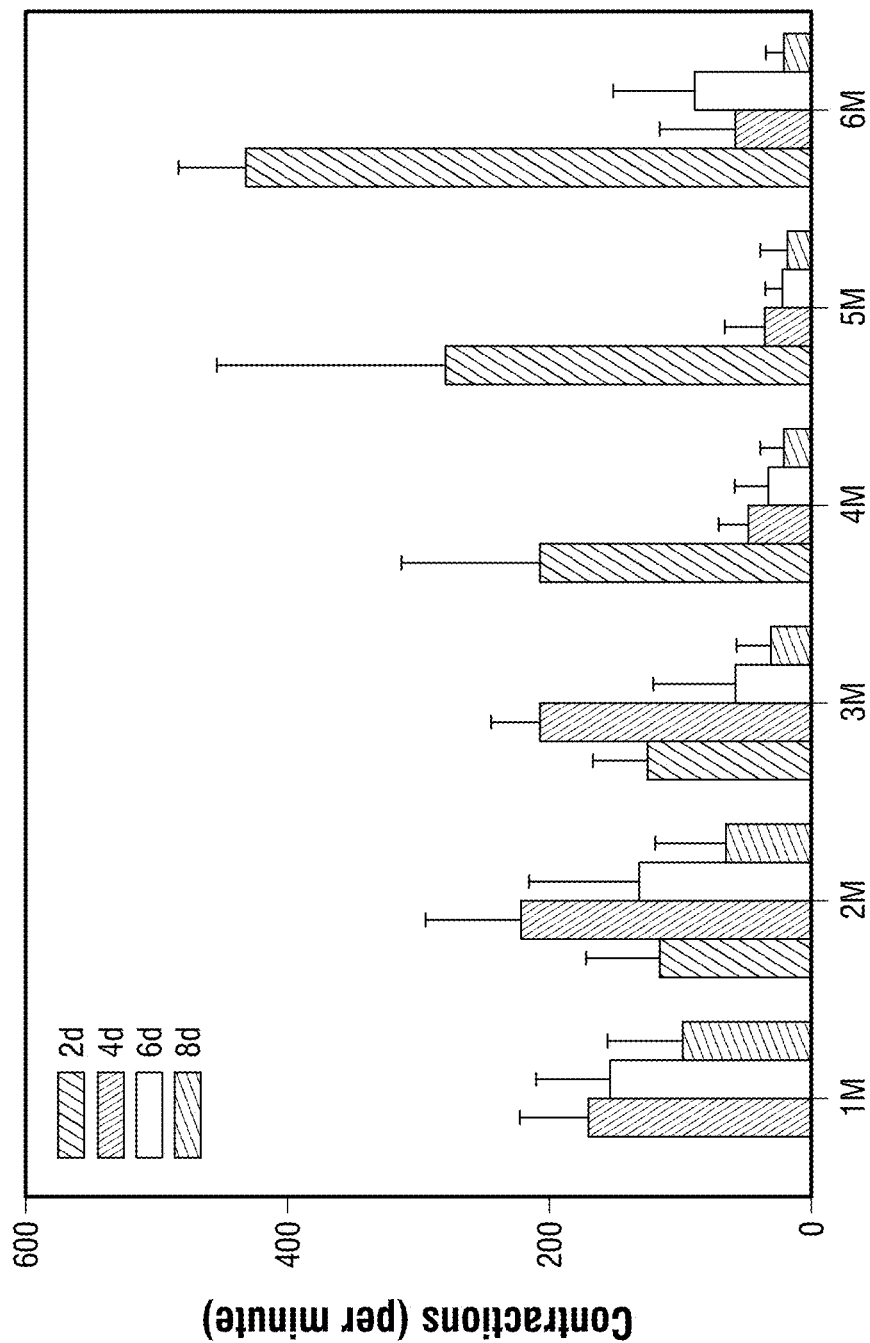
FIG. 3 shows the effect of using different cell densities over time, on the contraction frequency of the three-dimensional artificial cardiac patch. Contraction rates (bpm) measured and averaged for 1 to 6M density patches at 2, 4, 6, and 8 days.

The earlier spontaneous contractions in the cardiac patches were observed for a few of the patches with cell densities of 4M to 6M after only one day of incubation. The contraction rate at day 2 increased with higher cell densities. The average contraction rate for a 6M patch was 430±54 bpm (n=23) at day 2, which falls within the range of a normal adult rat heartbeat. For 1M to 3M densities, the highest mean contraction was at day 4 and then steadily decreased from day 6 to 8. For 4M to 6M densities, the highest contraction occurred much earlier, at day 2 but it decreased sharply from day 4 to 8 (FIG. 3).

A synchronized contraction relies on the appropriate proportion of cardiomyocytes to fibroblasts as well as smooth muscle cells and endothelial cells. In an exemplary embodiment of the present invention cardiac patches constructed with 1M to 3M cell densities maintained the appropriate cell-type proportion that enhanced the synchronization and increased the contraction rate. Because the fibroblasts proliferate faster than cardiomyocytes, after day 4 the appropriate proportion may no longer existed. The fibroblast overpopulation, thus, may be the cause for a decrease in contraction rate by affecting the initiation of pacemaker cells and delaying the propagation of action potential. Thus, synchronization slowed and the contraction rate decreased dramatically. The varying rates of proliferation between fibroblasts and cardiomyocytes may be a factor contributing to detection of steady contractions from patches constructed with 1M to 3M cell densities, and arrhythmic contractions from cardiac patch constructed from 4M to 6M cell densities.

Figure 4E:
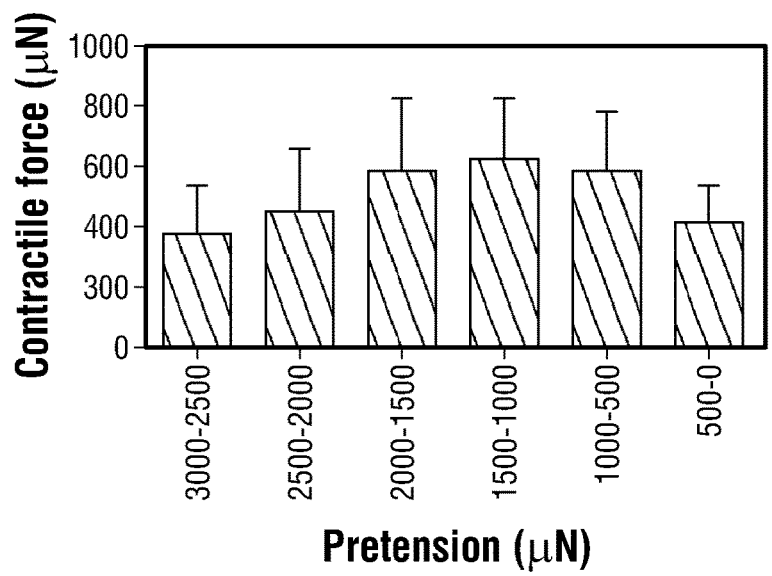

The strength of a muscle's contraction is influenced by the number of fibers within the muscle that have interactions of myosin cross bridges with actin, the rate of contraction, and the relaxed length of the muscle fibers. In an exemplary embodiment of the present disclosure, 1M to 3M patches exhibited steady contractions and 4M to 6M patches arrhythmic contractions. The contractile forces generated by 1M to 3M patches changed relative to pretension (baseline) (FIG. 4A). For example, the greatest contractile forces for 2M patches were generated with a pretension range of 500 to 2000 µN (FIG. 4E). Based on this preliminary pretension, the high and the low rate contractile forces of 1M to 6M patches were then recorded and averaged. One of the 4M patches spontaneously generated the greatest high rate contractile force (2141 µN) and the greatest low rate contractile force (2483 µN) without any treatment. The real muscle tissue layers of 4M and 6M patches were thicker than 2M (FIG. 7P); however, the signal volume indexes of collagen type I within the three densities were not significantly different. This suggests that the myofibril content in 4M to 6M patches may be higher than that in 2M patches. As such, the difference in myofibril content may explain the greater twitch forces generated from the 4 to 6M patches than the 2M. To determine the underlying mechanisms for arrhythmic contractions exhibited in 4M to 6M patches, the signal volume index of the gap junction protein Cx43 was examined. A statistical difference of Cx43 signal volume indexes in 4M and 6M patches was observed when compared with the 2M patches ($p<0.05$ or $p<0.01$) (FIG. 7Q). Cx43 is the major protein of cardiac ventricular gap junctions and is crucial to cell-cell communication and cardiac function. Recent works reported that changed expression of Cx43 might contribute to higher level of arrythmogenicity.

In some embodiments, the present disclosure provides a method for fabricating a three-dimensional artificial cardiac patch construct. Such a method is illustrated in FIG. 1 and may include one or more of the following steps: coating a substrate with an organic polymer; allowing the organic polymer coated on the substrate to air dry; mounting anchors on the organic polymer coating; sterilizing the coating of the organic polymer; forming a biodegradable gel-based support scaffold on top of the organic polymer; seeding neonatal cardiac cells on the biodegradable gel-based support scaffold; culturing the neonatal cardiac cells in vitro to form the three-dimensional artificial cardiac patch construct. In general the culture conditions used may be suitable for allowing the cells to self-organize into a real cardiac layer and detach from the substrate to form the three-dimensional cardiac patch. In some embodiments of the present disclosure, the organic polymer is a silicone elastomer. In some embodiments, the silicone elastomer is polydimethylsiloxane elastomer (PDMS). In some embodiments of the present disclosure, the biodegradable gel-based support scaffold is biocompatible and non-immunogenic. In some embodiments, the biodegradable gel-based support scaffold is fibrin. In some embodiments of the present disclosure, the seeding of the biodegradable gel-based support scaffold comprises layering the neonatal cardiac cells onto the scaffold. In some embodiments, the seeding of the biodegradable gel-based support scaffold comprises embedding the neonatal cardiac cells into the biodegradable gel-based support scaffold. In some embodiments, the neonatal cardiac cells are diluted in culture media prior to seeding on the biodegradable gel-based support scaffold. In some embodiments of the present disclosure, the real cardiac layer comprises the neonatal cardiac cells and naturally produced extracellular matrix on top of the biological support scaffold. In some embodiments, the thickness of the real cardiac layer is dependent on the density of the neonatal cardiac cells initially seeded. In some embodiments of the present disclosure, the fabricated artificial three-dimensional patch is spontaneously contractile. In some embodiments of the present disclosure, the artificial three-dimensional patch exhibits angiogenic bud formation. In some embodiments, the artificial three-dimensional patch exhibits active cell proliferation.

Further embodiments of the present disclosure pertain to a three-dimensional artificial cardiac patch made by the methods of the present disclosure. Additional embodiments of the present disclosure relate to a method of treatment of cardiac tissue injury in a subject in need thereof utilizing the three-dimensional artificial cardiac patch construct disclosed herein.

As set forth in detail herein, the methods and compositions of the present disclosure have numerous embodiments and variations. In particular, various types of organic polymers may be used to coat the substrate. Likewise, various types of biodegradable gel-based support scaffolds may be formed on top of the organic polymer coating. In addition, various types of cardiac cells may be seeded in the support scaffold. Furthermore, the density of the cardiac cells seeded may be varied to modulate the thickness of the patch formed, the rate as well as the force of contraction.

Organic Polymers

In some embodiments of the present disclosure, the organic polymer may be a silicone elastomer. In a related embodiment the silicone elastomer may be polydimethylsiloxane elastomer (PDMS). In some embodiments, anchors may be mounted on the organic polymer coating and secured to the substrate. Suitable anchors that may be used include minutien pins.

Cells

In a preferred embodiment, the cell types that may be used to generate the three-dimensional artificial cardiac patch construct of the present disclosure may include, but are not limited to, cardiomyocytes, endocardial cells, cardiac adrenergic cells, cardiac fibroblasts, vascular endothelial cells, smooth muscle cells, stem cells, cardiac progenitor cells, and myocardial precursor cells. Depending on the application of the three-dimensional artificial cardiac patch and the type of cardiac tissue material that is desired, the above types of cells may be used independently or combined with one another. In one embodiment, the three-dimensional artificial cardiac patches may be composed of primary tissue isolates from the heart. Accordingly, small samples of autologous, allogenic or xenogeneic donor cells may be used for fabricating the three-dimensional artificial cardiac patch construct. Alternatively, cells such as non-immunogenic universal donor cell lines or stem cells may be used so long as they can be manipulated to form the three-dimensional artificial cardiac patch construct.

In certain embodiments, stem cells useful for the compositions and methods provided herein include, for example, embryonic stem cells, amniotic stem cells, bone marrow stem cells, placenta-derived stem cells, embryonic germ cells, cardiac stem cells, CDCs, induced pluripotent stem cells, mesenchymal stem cells, endothelial progenitor cells, and spermatocytes. The stem cells employed can be autologous or heterologous to the subject being treated. In specific embodiments, the stem cells are autologous stem cells.

The stem cells can be obtained or derived from any of a variety of sources. For example, subjects that can be the donors (or recipients) of stem cells in the methods and compositions presented herein include, for example, mammals, such as non-primates (e.g., cows, pigs, horses, cats, dogs, rats or rabbits) or primates (e.g., monkeys or humans). In specific embodiments, the subject is a human. In one embodiment, the subject is a mammal, e.g., a human, such as a human with a congenital heart defect or acute or chronic heart failure or other cardiac tissue injury.

In a preferred embodiment of the present disclosure, freshly isolated neonatal cardiac cells may consist of fibroblasts, cardiomyocytes, smooth muscle cells, endothelial cells and cardiac stem cells. The proliferation rate of cardiac cells is higher in the fetal stage than that in the neonatal stage, and greatly diminishes in adulthood. In an embodiment of the present disclosure, 2-3-day-old rat pup heart cells may be used to construct the three-dimensional artificial cardiac patch disclosed herein.

Biodegradable Gel-Based Support Scaffolds

Biodegradable gel-based support scaffolds that may be used to generate the three-dimensional artificial cardiac construct of the present disclosure may include, but are not limited to collagen, alginate, chitosan, fibrin, fibronectin, matrigel, small intestine submucosa, and acellular tissue.

In some embodiments of the present disclosure the biodegradable gel-based support scaffold may be biocompatible or non-immunogenic. In a preferred embodiment the biodegradable gel-based support scaffold may be fibrin. Fibrin is a natural self-assembling biopolymer with many interesting properties, such as biocompatibility, bioresorbability, ease of processing, ability to be tailored to modify the conditions of polymerization, and potential for incorporation of both cells and cell mediators. Fibrin is used by the body to form clots along damaged endothelium. Fibrin gels possess high seeding efficiency, uniform cell distribution, and adhesion capabilities. Fibrin alone, or in combination with other materials, has been used as a biological scaffold for stem and primary cells to regenerate adipose tissue, bone, cardiac tissue, cartilage, liver, nervous tissue, ocular tissue, skin, tendons, and ligaments.

In an embodiment, the fibrin is formed by mixing thrombin and fibrinogen solutions. In an embodiment of the present disclosure the biodegradable gel-based support scaffold is also non-immunogenic. Thrombin and fibrinogen which react to form fibrin gel can be produced from the recipient's own blood, thus no the potential risk of foreign body reaction or infection will occur when used as a component in clinical application. In an embodiment of the present disclosure, the fibrin support scaffold may be developed with human fibrinogen and thrombin and its physical properties may be characterized by histology and immunohistochemistry.

In some embodiments of the present disclosure the neonatal cardiac cells may be layered on to the biodegradable gel-based support scaffold. In an alternative embodiment, the neonatal cardiac cells may be embedded into the biodegradable gel-based support scaffold.

In a related embodiment the neonatal cardiac cells may be diluted in culture media prior to seeding on the biodegradable gel-based support scaffold.

In an exemplary embodiment, the width of cardiomyocytes from adult rats aged from 8 to 24 weeks was quantified to be 26.1-30.6 μm, and the length as 123.3-148.8 μm. In an embodiment of the present disclosure, the pore sizes of the fibrin support scaffold in the three-dimensional artificial cardiac patch, were 15.0-150.0 μm (FIGS. 6A and 6B), which is a suitable compartment for a cardiomyocyte that may facilitate cell organization and interconnectivity.

In some embodiments the present disclosure provides for the formation of a real cardiac layer on top of the biological support scaffold. In a related embodiment, the real cardiac layer may include the neonatal cardiac cells and naturally produced extracellular matrix on top of the biological support scaffold. Such a layer of cells is illustrated in FIGS. 7A-7C. In a preferred embodiment, the thickness of the real cardiac layer formed may be modulated by varying the density of the cells layered or embedded in the biodegradable gel-based support scaffold. The reason for this difference may result from the lower cell density and/or the different growth rate of each cell type within the patch. In an exemplary embodiment, the optimal cell density, using rat neonatal cardiac cells, for the formation of the three-dimensional artificial cardiac patch may be 4 million (4M).

In an embodiment of the present disclosure the three-dimensional artificial cardiac patch is spontaneously contractile. In a preferred embodiment, the rate of spontaneous contraction of the cardiac patch may be dependent on the density of the neonatal cardiac cells initially seeded. In a related embodiment, the three-dimensional artificial cardiac patch may exhibit contractile twitch force. In a preferred embodiment the contractile twitch force may me modulated by varying the density of the neonatal cardiac cells initially seeded. In some embodiments of the present disclosure, the three-dimensional artificial patch may exhibit angiogenic bud formation. Further, in an embodiment of the present disclosure, vascularity of the three-dimensional artificial cardiac patches may be determined by staining for various endothelial cell markers to show presence of angiogenesis buds capable of facilitating media perfusion. The microvasculature within the patch may be suitable to supply blood and nutrients into the patch during in vivo applications.

In related embodiments of the present disclosure, the three-dimensional artificial cardiac patch may exhibit active cell proliferation. The viability of freshly isolated heart cells may be determined by using established isolation protocols. Furthermore, in another embodiment of the present disclosure, the proliferation of the cells within the three-dimensional artificial cardiac patch may be assessed by staining for somatic cell proliferation markers. In an embodiment, the somatic cell proliferation marker stained for is the Ki67 nuclear and nucleolar protein.

In some embodiments the present disclosure provides for implanting the fabricated three-dimensional artificial cardiac construct in a suitable recipient. In a related embodiment, the recipient may be suffering from a congenital heart disease. In an embodiment the congenital heart disease is selected from a group consisting of Hypoplastic left heart syndrome, tetralogy of fallot, ventricular septal defects, atrial septal defects, endocardial cushion defect. In another embodiment, the recipient may be suffering from a cardiac tissue injury. In a preferred embodiment, the cardiac tissue injury may be caused by acute or chronic stress, atheromatous disorders of blood vessels, ischemia, myocardial infarction, inflammatory disease and cardiomyopathies or myocarditis. In some embodiments, the present disclosure provides a method for the treatment of a cardiac tissue injury. Such a method may include implanting the three-dimensional cardiac construct disclosed herein in a subject in need thereof. In a related embodiment the cardiac tissue injury may be due to acute or chronic stress, atheromatous disorders of blood vessels, ischemia, myocardial infarction, inflammatory disease and cardiomyopathies or myocarditis. In some embodiments, the acute or chronic stress may be due to systemic hypertension, pulmonary hypertension or valve dysfunction. In some embodiments of the present disclosure, the atheromatous disorder of blood vessels is coronary artery disease.

In another embodiment of the present disclosure, there is provided a composition comprising the three-dimensional artificial cardiac patch disclosed herein. In an embodiment the present disclosure pertains to a three-dimensional artificial cardiac patch comprising an organic polymer coated on a substrate; a biodegradable gel-based support scaffold formed on top of the organic polymer; and cardiac cells, where the cardiac cells are seeded on the biodegradable gel-based scaffold. In an embodiment, the three-dimensional artificial cardiac patch further comprises at least one agent from the group consisting of survival factors, growth factors, pharmacological agents, angiogenic factors, beta-blockers or ACE inhibitors.

In a related embodiment there is also provided a medicament. Such a medicament includes the three-dimensional artificial cardiac patch disclosed herein. In a related embodiment, the medicament of the present disclosure further comprises at least one agent from the group consisting of survival factors, growth factors, pharmacological agents, angiogenic factors, beta-blockers or ACE inhibitors.

In an exemplary embodiment of the present disclosure, the three-dimensional artificial cardiac patch may be fabricated using 2-3-day-old rat pup heart cells on a fibrin gel-based support scaffold. In a related embodiment, modulation of the contraction rate of the three-dimensional artificial cardiac patch by varying the density of the cells embedded in or layered on the fibrin gel was observed. The spontaneous contractions in the three-dimensional artificial cardiac patches were recorded and measured at day 2 from the cell densities of 2 million (2M) to 6 million (6M). Earlier tissue contractions were observed for a few of the patches with cell densities of 4 million (4M) to 6 million (6M) after only one day of incubation. The contraction rate at day 2 increased with higher cell densities. The average contraction rate for a 6M patch was 430±54 bpm (n=23) at day 2, which falls within the range of a normal adult rat heartbeat. For 1 to 3M densities, the highest mean contraction was at day 4, and then steadily decreased from day 6 to 8. For 4 to 6M densities, the highest contraction occurred much earlier, at day 2, but it decreased sharply from day 4 to 8 (FIG. 3).

In the exemplary embodiment, the real cardiac layers formed for 4M and 6M patches were thicker than 2M (FIG. 7N). The same signal volume indexes of collagen type I within the three densities suggest that the myofibril content in 4 to 6M patches was higher than that in 2M patches. As such, the difference in myofibril content may explain the greater twitch forces generated from the 4 to 6M patches than the 2M. To determine the underlying mechanisms for arrhythmic contractions exhibited in 4 to 6M patches, Applicants examined the signal volume index of the gap junction protein Cx43. Cx43 is the major protein of cardiac ventricular gap junctions and is crucial to cell-cell communication and cardiac function. Recent works reported that reduced expression and enhanced lateralization of Cx43 might contribute to enhanced arrythmogenicity. In an exemplary embodiment, no statistical difference of Cx43 signal volume index in 4M and 6M patches was observed as compared to 2M ones, yet, there was a slight trend showing that the expression of Cx43 was relatively higher in 2M patches (FIG. 7P).

In an exemplary embodiment, the amplitude of contractile twitch force generated and the onset and rate of contractions was modulated with cell densities. The patch with 4 million cells generated the greatest high and low rate contractile twitch forces, and the contraction rate of a patch with 6 million cells resembled an adult rat heart rate, which, as of yet, were the best reported. In addition, patches manifested flourishing angiogenesis and cellular division. Further modulation is needed to enable media perfusion throughout the entire patch, and will result in a more robust 3D artificial cardiac patch Advantages The methods of the present disclosure may be utilized to make three-dimensional artificial cardiac patches for various applications. For instance the methods of the present disclosure may be used for repairing cardiac tissue injuries and congenital heart defects. The methods of the present disclosure may also be used for the development of biocompatible, adaptive, non-immunogenic materials for cardiac tissue replacement. The three-dimensional artificial cardiac patches of the present disclosure revealed better contractility than ever reported before for engineered cardiac tissue. Additionally, the cardiac patches of the present disclosure display abundant vascularization and robust cellular division. Furthermore, in some embodiments of the present disclosure, the patches may be constructed using host origin fibrinogen and thrombin to produce the non-immunogenic fibrin scaffold before in vivo application.

Reference will now be made to various embodiments of the present disclosure and experimental results that provide support for such embodiments. However, Applicants note that the disclosure herein is for illustrative purposes only and is not intended to limit the scope of the claimed subject matter in any way.

Example 1

Isolation of Primary Cardiac Cells

Cardiac cells were isolated from the hearts of 2-3 day old neonatal Sprague-Dawley rats using an established method. Briefly, each heart was cut into 3-4 pieces in an ice-cold phosphate buffer consisting of 116 mM NaCl, 20 mM HEPES, 1 mM $Na_2HPO_4$, 5.5 mM glucose, 5.4 mM KCl and 0.8 mM $MgSO_4$. After blood cells were rinsed out, heart pieces were transferred to a dissociation solution (DS) consisting of 0.32 mg/ml collagenase type 2-filtered (Worthington Biochemical Corporation, Lakewood, N.J.) and 0.6 mg/ml pancreatin in phosphate buffer. The hearts were cut into 1 $mm^2$ pieces and then transferred to an orbital shaker and maintained at 37° C. for 30 minutes at 60 rpm. At the end of the digestion process, the supernatant was collected in 3 ml of horse serum to neutralize the enzyme and centrifuged at 1000 rpm for 5 minutes at 4° C. The cell pellet was resuspended in 5 ml horse serum and kept in an incubator at 37° C. supplied with 5% $CO_2$. Fresh DS was added to the partially-digested tissue and the digestion process was repeated an additional 2-3 times. Cells from all the digests were pooled, centrifuged and suspended in culture medium (CM) consisting of 320 ml M199 (Life Technologies, Grand Island, N.Y.), with 20% F12k (Life Technologies, Grand Island, N.Y.), 10% fetal bovine serum, 5% horse serum, 1% antibiotic-antimycotic, 40 ng/ml hydrocortisone and insulin 100 ng/ml. Cell viability was analyzed by Trypan blue solution (4%) staining according to the manufacturer's protocol and the percentage of live cells determined.

Example 2

Fabrication of Artificial Cardiac Patch

The method to fabricate the cardiac patch is shown in FIGS. 1A-1H. Briefly, a 35 mm tissue culture plate was coated with 2 ml of SYLGARD (PDMS, type 184 silicone elastomer) (Dow Chemical Corporation, Midland, Mich.). The plate was air dried for 2 weeks and sterilized with 80% ethanol before use. Four minutien pins (Fine Science Tools, Foster City, Calif.), 0.1 mm diameter, were placed in the culture plate to form a 2 cm×2 cm square. The fibrin gel was made by plating 1 ml of CM containing 10 U/ml thrombin and adding 500 µl of saline containing 20 mg/ml fibrinogen, and well mixed to promote the formation of gel within 15 minutes. Primary cardiac cells were diluted in CM at a pre-set density and 2 ml of the cell suspension CM was transferred to the culture plate. Aminocaproic acid (2 mg/ml) was added to the culture plate to inhibit the fibrinolysis by endogenous proteases. The cells were cultured in an incubator at 37° C. and 5% $CO_2$ with CM changes every other day.

Example 3

Patch Formation and Contraction Rate

Figure 8:
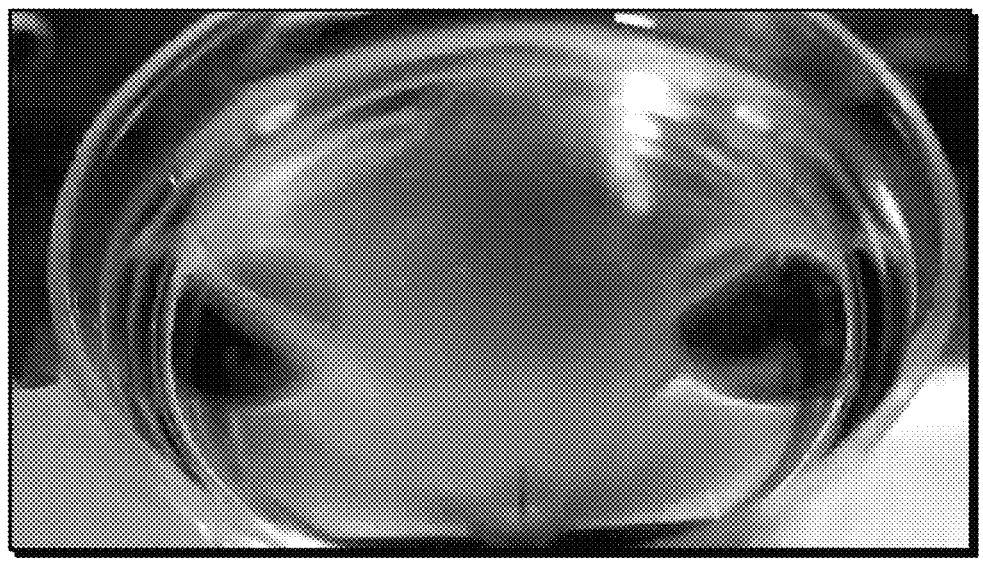
FIG. 8 is a representation of a movie from 6M patches at day 3, taken inside the incubator (448 bpm), under the microscope (448 bpm) and then on the bench.

Two days after cell plating, cultured cardiac constructs began contraction and fibrin gels detach from the rim of culture plates. At days 2, 4, 6, and 8, the patch growth progress was captured in still photographs and videos using a camera (Lumena, Ottawa, ON) mounted on an inverted phase-contrast microscope (Olympus, Center Valley, Pa.). The movies were slowly replayed and the contraction rates manually counted (FIG. 8 showing Movie 1).

Example 4

Contractile Twitch Force and Electrocardiogram (ECG)

From day 4, twitch force was measured using a high sensitivity isometric force transducer (MLT0202, ADinstruments, Colorado Springs, Colo.), connected to a quad bridge amplifier (FE224, ADinstruments, Colorado Springs, Colo.), electrophysiological signal was measured using Octal Bio Amp (ML138, ADinstruments, Colorado Springs, Colo.). Data was acquired through a 16 channel PowerLab system (PL3516/P, ADInstruments, Colorado Springs, Colo.). As shown in FIG. 1J, the contractile force was measured by attaching the force transducer arm to one free-corner of the square patch, while the other three ends were held fixed. In order to obtain the Frank-Starling relationship of contractile force, pretension was adjusted using a micro-manipulator (Radnoti LLC, Monrovia Calif.) and measurements of spontaneous contraction were recorded. Electrocardiogram (ECG) of the patch was measured by inserting the cathode into the center of the patch and the anode in one of the four patch corners. The media immersing the patch was used as ground. Spontaneous contractile force and ECG measurements were recorded for 30-60 seconds. LabChart (ADInstruments, Colorado Springs, Colo.) was used for data analysis. The peak analysis module was used to calculate the maximum twitch force and baseline force (pretension). The ECG analysis module was used to calculate the R wave amplitude.

Example 5

Morphology

Seven days after plating, formed patches were trimmed, and from the central part of the patch two 0.5×0.5 cm blocks were taken, placed in a peel-a-way disposable embedding mold (VWR International, Radnor, Pa.) and frozen in liquid nitrogen, and then immediately, immerged in Tissue Tek OCT compound (VWR International, Radnor, Pa.), and immediately placed in a −80° C. freezer. Once the OCT compound was completely solid, each sample was sliced using a cryotome (Thermo Fisher Scientific, Waltham, Mass.). Tissue cross- and planar-sections were cut at a thickness of 10 µm or 6 µm. The sections were placed on VWR® Microslides for preparation of morphological and immunofluorescence examinations. For measurement of physical properties such as fibrin scaffold thickness and pore size, images from both cross- and planar-sections of 6 µm thickness were taken directly under a light microscope (Olympus, Center Valley, Pa.) and fibrin scaffold thickness was calculated with ImageJ 1.47d (Wayne Rashand, National Institute of Health, USA). For measurement of the real heart tissue (a layer of cells and naturally produced extracellular matrix forms on top of the fibrin gel scaffold) thickness on the fibrin scaffold, cross- and planar-sections of 10 µm thickness were stained with Masson's trichrome reagents according to manufacturer's protocol and images were taken under a light microscope. The distinct tissue layers were traced and thicknesses calculated.

Example 6

Immunofluorescence

For measurement of the signal volumes of connexin 43 and collagen type I, 6 µm thickness cross-sections were fixed in ice cold acetone for 10 minutes, nonspecific epitope antigens were blocked with 10% goat serum at room temperature for 1 hour. Sections were incubated with specific mouse anti-α-actinin monoclonal antibody (Sigma, Catalog No A7811) 1:200, rabbit anti-connexin 43 (Cx43) (Abcam, ab11370) 1:100, rabbit anti-von Willebrand factor (vWF) (Abcam, ab6994) 1:750, rabbit anti-ki 67 (Abcam, ab66155) 1:100, rabbit anti-collagen type I (Abcam, ab34710) 1:100 at room temperature for 1 hour, and treated with goat anti-mouse and goat anti-rabbit secondary antibodies (Alexa Fluor 488, Alexa Fluor 546, and Alexa Fluor 633, Life Technology) 1:400 at room temperature for 1 hour. Nuclei were counterstained with DAPI (2.5 µg/ml) for 5 min at room temperature. For observation of endothelial cell growth and nuclear division in the patch, a modified immunostaining protocol of tissue constructs was used. Fresh tissue patches were directly fixed in ice cold acetone for 10 minutes. 1.0×1.0 tissue patch blocks from the central part of the patches were trimmed and nonspecific epitope antigens were blocked and cell membranes permeated with 10% goat serum per 0.5% Triton X-100 at room temperature for 45 minutes. Tissue patch blocks were then incubated in mouse anti-a-actin antibody 1:200, rabbit anti-von Willebrand factor (vWF) (Abcam, ab6994) 1:750, rabbit anti-ki67 (Abcam, ab66155) 1:100, and rabbit anti-Cx43 1:100 at room temperature for 2 hours. The rest of the steps of immunostaining for tissue patches were same as that for cross-sections. Fluorescent images were obtained with a Nikon C2$^+$ confocal laser scanning microscope (Nikon Instruments Inc. Melville, N.Y.). For measurement of the changes of gap junctions, collagens and myofibrils, signal volumes of Cx43, collagen type I and α-actinin were examined within cross-sections. Two movies from each sample were acquired with a signal depth of 8 µm scanned by 33 frames. After determining specific thresholds for Cx43, collagen type I and α-actinin, signal volume and intensity for each sample were measured. The relative changes of Cx43 (or collagen type I) for different cell densities were expressed with Cx43 Index=(Cx43 volume*intensity)/(α-actinin volume*intensity)

and averaged for each sample.

Example 7

Statistics

Results are presented as mean±standard deviation. Chi-Square analysis was used to test frequency variables. Comparisons among the three groups were made with a one-way analysis of variance (ANOVA), followed by the Bonferroni post hoc comparison test; in addition, Kruskal-Wallis test were performed. In all tests, differences were considered statistically significant at a value of $p<0.05$.

Example 8

Patch Formation

Figure 2:
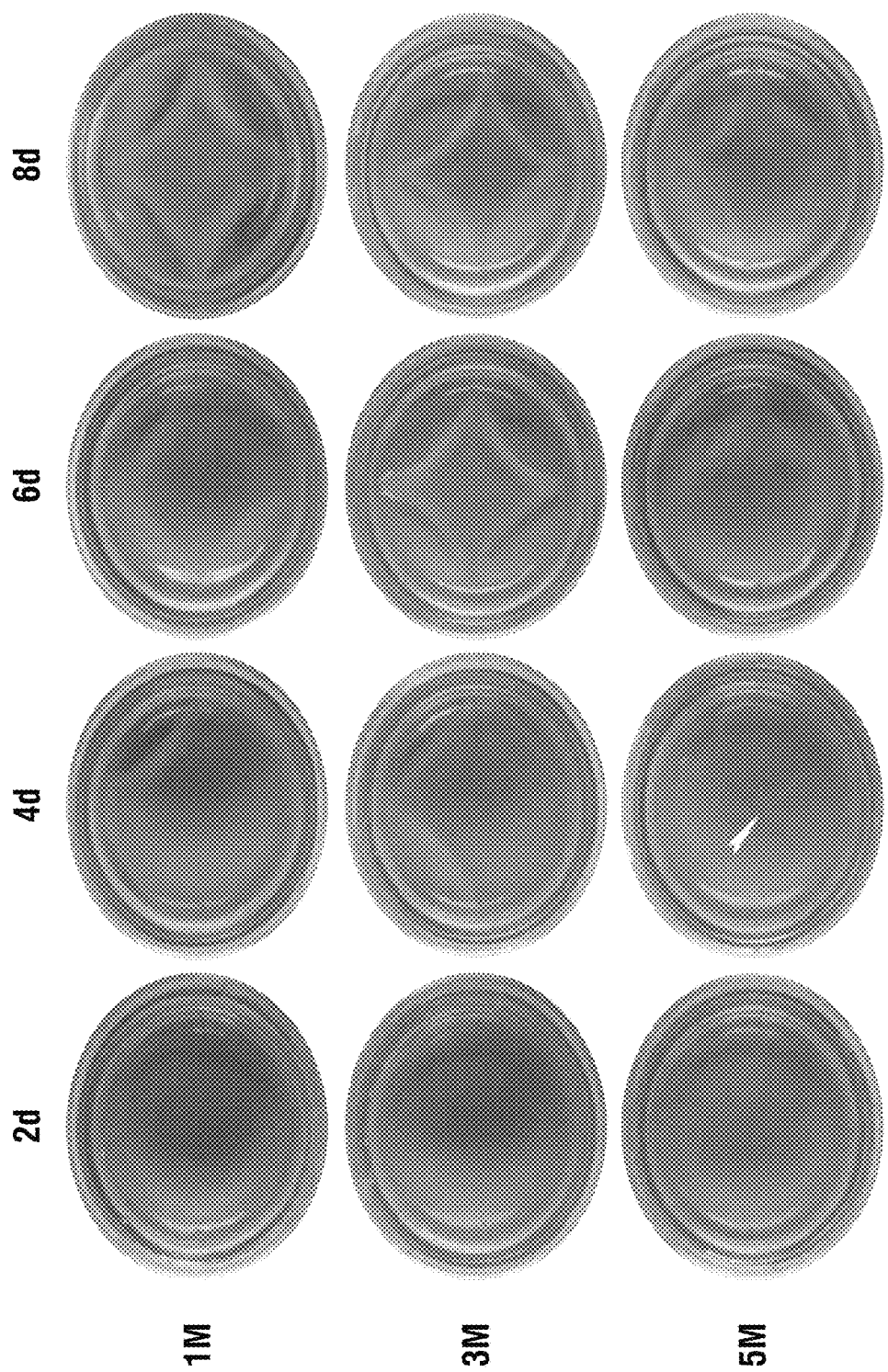
FIG. 2 shows the effect of using different cell densities over time on the formation of the three-dimensional artificial patch construct. The tissue begins to detach at 4 days for the 5M patch.

By the present established isolation method, cell viability was 81.0±2.2% (n=16). The time required for patch formation was a function of the initial plating density. Representative progression of patch formation of 1, 3 and 5 million cells (M) per dish is shown in FIG. 2. At day 4, formation was complete for 28.0% (7/25), 56.3% (9/16), and 40.0% (6/15) of patches formed with 1, 3 and 5M densities, respectively; Pearson Chi-Square analysis indicated p=0.195. At day 6, there were 68.0% (17/25), 87.5% (14/16), and 60.0% (9/15) of patches formed with 1, 3 and 5M densities, respectively; Fisher's Exact test demonstrated p=0.232. The results indicated that though there were no statistical differences among the plating densities, patches with 3M density exhibited the highest percentage of patch formation both at days 4 and 6. From day 4 the tissue detachments were seen in the 5M and 6M density patches (arrow in FIG. 2).

Example 9

Contraction Rate

From day 2 the spontaneous tissue contractions were seen under microscope from the dishes with 2M-6M densities. The average contraction rates for 2, 3, 4, 5 and 6M were 115±56 (n=27), 124±42 (n=16), 207±107 (n=23), 279±174 (n=8) and 430±54 bpm (n=23) respectively; Kruskal-Wallis test showed significant differences ($p<0.01$) with mean ranks 27.8, 32.7, 48.7, 57.0 and 82.7 respectively. At day 4 the average contraction rates for 1, 2, 3, 4, 5 and 6M were 169±54 (n=25), 222±74 (n=37), 207±38 (n=16), 48±23 (n=17), 35±31 (n=12) and 57±59 bpm (n=14) respectively; Kruskal-Wallis test analyzed significant difference ($p<0.01$) with mean ranks 69.2, 87.3, 87.0, 26.5, 18.3 and 25.7 respectively. Then the average contraction rates for each cell density decreased at days 6 and 8 (FIG. 3).

Example 10

Contractile Twitch Force

High rate (65-270 bpm) and low rate (<20 bpm) twitch forces were recorded from formed patches from day 4 to 6. For 1, 2 and 3M patches, the high rate rhythmic contractions were detected throughout the entire recording period (starting at the onset of pretension); the largest twitch force was recorded when the pretension was set between 500 to 2000 µN (FIGS. 4A, 4B). However, for 4, 5 and 6M patches, high rate contractions were only detected within the a few seconds after a pretension load was applied, after which low rate contractions were observed (FIG. 4C, 4D). FIG. 4E illustrates the effects of pretension on the magnitude of contractile force for 2M density patches. For, the pretension ranges of 3000-2500, 2500-2000, 2000-1500 1500-1000, 1000-500 and 500-0 µN, the contractile forces were 377±154 µN (n=4), 445±213 µN (n=8), 583±238 µN (n=8), 621±200 µN (n=8), 584±195 µN (n=8) and 409±126 µN (n=8), respectively (Bonferroni post hoc p>0.05 for all).

Figure 4F:
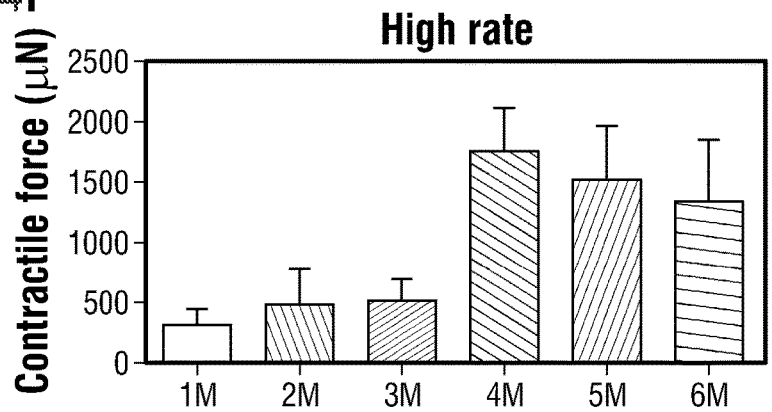
Figure 4G:
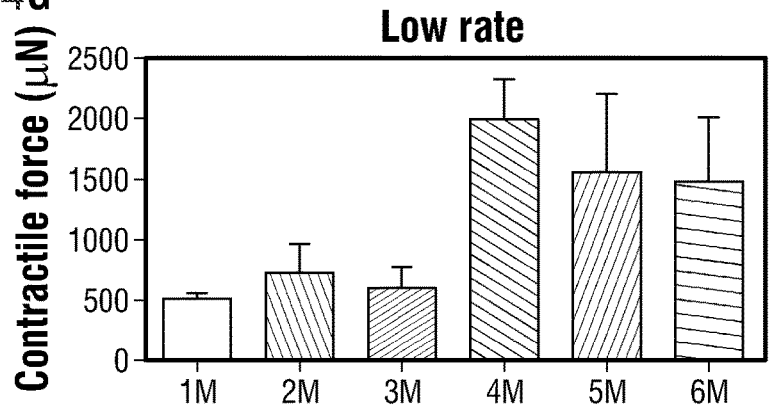

Representative samples of the greatest high and low rate contractile forces recorded by a pretension range of 1000 to 2000 µN from 2, 4 and 6M densities are shown in FIG. 4B, FIG. 4C and FIG. 4D. The maximum high rate contractile forces were 932, 2160 and 2141 µN and the maximum low rate contractile forces were 1044, 2483 and 2364 µN for 2, 4 and 6M, respectively. The average high rate contractile forces for 1 through 6M patches loaded with a pretension range of 1000 to 2000 µN showed a significant difference (Kruskal-Wallis $p<0.01$). The 1-3M patches had an average contractile force in the 300-500 µN ranges, whereas the 4-6M patches possessed a contractile force in the 1300-1700 µN ranges, with the 4M patch showing the highest contractile force (FIG. 4F). The average low rate twitch forces for 1 to 6M patches loads with pretension between 1000 and 2000 µN also showed a significant difference (Kruskal-Wallis $p<0.01$). The 1-3M patches had an average contractile force in the 1500-2000 µN ranges, with the 4M patch showing the highest contractile force (FIG. 4G).

Electrocardiogram

Figure 5:
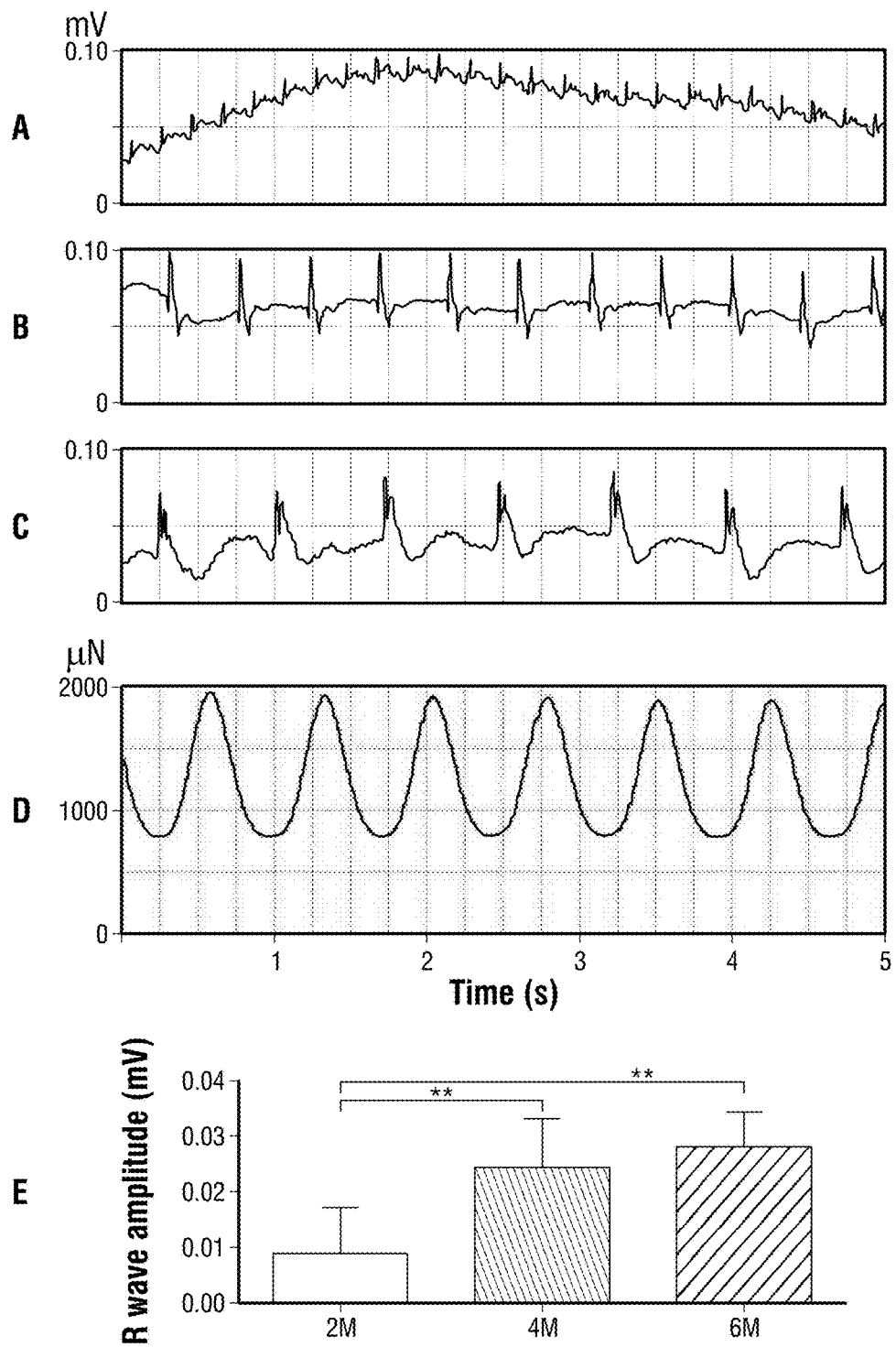
FIGS. 5A-5E show contractile force generated by the fabricated three-dimensional artificial cardiac patch as a function of cell density.

The representative ECG graphs for 2, 4 and 6M patches with high rate contraction are shown in FIGS. 5A-5C. FIG. 5D is the synchronized contraction graph of the 6M patch. The QRS complex pattern from 2 and 4M patches closely resembles that of an adult rat heart. The R-wave amplitudes from 4M (0.0244±0.0087, n=10) and 6M (0.0281±0.0064 mV, n=5) patches were greater than that from 2M (0.0089±0.0081 Mv, N=8) patch (Bonferroni post hoc p<0.001).

Example 11

Morphology

The physical properties of fibrin gel scaffolds of formed patches were examined at day 7 (FIG. 6). A layer of cardiac cells and self-produced extracellular matrix proteins, which comprises the real cardiac layer, formed on top of the fibrin gel scaffold (FIG. 6A). The total cross-sectional depth of the patches was 700-1000 μM (FIG. 6A) and the planar networks of the fibrin gel scaffolds are depicted in FIGS. 6B and 6C. The thickness (FIG. 6D) and planar texture (FIGS. 6E and 6F) of the real cardiac layer were further revealed by Masson trichrome staining though they were physically altered by fixing process. The planar section shows that the real cardiac tissue is closely incorporated into the lower fibrin network (FIG. 6E). The positive staining for the ki67 (white) (FIGS. 6G and 6H) suggests the presence of robust nuclear division, the positive staining for vWF (red) (FIGS. 6G and 6I) suggests that endothelial cells were proliferating, and the positive staining for connexin 43 (yellow) (FIG. 6I) indicates intracellular coupling via gap junctions in the artificial tissue.

Samples stained with Masson's trichrome were used to illustrate the thickness of muscle tissue and support fibrin scaffold, as shown in FIGS. 7A, 7B and 7C from patches with 2, 4 and 6M densities. Cross-sections in FIGS. 7D-7O show the expressions of myofibrils by α-actinin staining and gap junctions by Cx43 staining for 2, 4 and 6M. The average thicknesses of real muscle layers were 18.2±2.4 (n=13), 21.4±1.4 (n=14) and 20.6±2.4 (n=12), respectively; there were significant differences when comparing 4M and 6M (Bonferroni post hoc p<0.05 or p<0.01) with 2M (FIG. 7P). The signal volume index of Cx43 was greater for 2M (0.182±0.051, n=13), than for 4M (0.132±0.039, n=13) and 6M (0.126±0.038, n=16) (Bonferroni post hoc p<0.05 or p<0.01) (FIG. 7Q). The signal volume index of collagen type I was also calculated to be (0.221±0.065, n=9), (0.209±0.070, n=8) and (0.196±0.050, n=15) for 2M, 4M and 6M, respectively; however, there were no obvious trends or significant statistical differences (Bonferroni post hoc p>0.05).

In summary, Applicants report the fabrication of a three-dimensional artificial cardiac patch using neonatal heart cells on a fibrin gel scaffold. The amplitude of contractile twitch force generated and the onset and rate of contractions was modulated with cell densities. The patch with 4 million cells generated the greatest high and low rate contractile twitch forces, and the contraction rate of a patch with 6 million cells resembled an adult rat heart rate, which, as of yet, were the best reported. In addition, patches manifested flourishing angiogenesis and cellular division.

The embodiments described herein are to be construed as illustrative and not as constraining the remainder of the disclosure in any way. While the embodiments have been shown and described, many variations and modifications thereof can be made by one skilled in the art without departing from the spirit and teachings of the invention. Accordingly, the scope of protection is not limited by the description set out above, but is only limited by the claims, including all equivalents of the subject matter of the claims. The disclosures of all patents, patent applications and publications cited herein are hereby incorporated herein by reference, to the extent that they provide procedural or other details consistent with and supplementary to those set forth herein.

REFERENCES

[1] Risbud M. Tissue engineering: implications in the treatment of organ and tissue defects. Biogerontology 2001; 2:117-25.

[2] Wei H J, Chen C H, Lee W Y, Chiu I, Hwang S M, Lin W W, et al. Bioengineered cardiac patch constructed from multilayered mesenchymal stem cells for myocardial repair. Biomaterials 2008; 29:3547-56.

[3] Wollert K C, Drexler H. Cell therapy for the treatment of coronary heart disease: a critical appraisal. Nat Rev Cardiol 2010; 7:204-15.

[4] Sekine H, Shimizu T, Dobashi I, Matsuura K, Hagiwara N, Takahashi M, et al. Cardiac cell sheet transplantation improves damaged heart function via superior cell survival in comparison with dissociated cell injection. Tissue Eng Part A 2011; 17:2973-80.

[5] Porrello E R, Mahmoud A I, Simpson E, Hill J A, Richardson J A, Olson E N, et al. Transient regenerative potential of the neonatal mouse heart. Science 2011; 331:1078-80.

[6] Zimmermann W H, Fink C, Kralisch D, Remmers U, Weil J, Eschenhagen T. Three-dimensional engineered heart tissue from neonatal rat cardiac myocytes. Biotechnol Bioeng 2000; 68:106-14.

[7] Black L D, 3rd, Meyers J D, Weinbaum J S, Shvelidze Y A, Tranquillo R T. Cell-induced alignment augments twitch force in fibrin gel-based engineered myocardium via gap junction modification. Tissue Eng Part A 2009; 15:3099-108.

[8] Fujimoto K L, Clause K C, Liu L J, Tinney J P, Verma S, Wagner W R, et al. Engineered fetal cardiac graft preserves its cardiomyocyte proliferation within postinfarcted myocardium and sustains cardiac function. Tissue Eng Part A 2011; 17:585-96.

[9] Swartz D D, Russell J A, Andreadis S T. Engineering of fibrin-based functional and implantable small-diameter blood vessels. Am J Physiol Heart Circ Physiol 2005; 288:H1451-60.

[10] Guyette J P, Fakharzadeh M, Burford E J, Tao Z W, Pins G D, Rolle M W, et al. A novel suture-based method for efficient transplantation of stem cells. J Biomed Mater Res A 2012. Available from URL: http://www.ncbi.nlm.nih.gov/pubmed/22961975 (doi: 10.1002/jbm.a.34386)

[11] Baar K, Birla R, Boluyt M O, Borschel G H, Arruda E M, Dennis R G. Self-organization of rat cardiac cells into contractile 3-D cardiac tissue. FASEB J 2005; 19:275-7.

[12] Huang Y C, Khait L, Birla R K. Contractile three-dimensional bioengineered heart muscle for myocardial regeneration. J Biomed Mater Res A 2007; 80:719-31.

[13] Barsotti M C, Felice F, Balbarini A, Di Stefano R. Fibrin as a scaffold for cardiac tissue engineering. Biotechnol Appl Biochem 2011; 58:301-10.

[14] Ahmed T A, Dare E V, Hincke M. Fibrin: a versatile scaffold for tissue engineering applications. Tissue Eng Part B Rev 2008; 14:199-215.

[15] Bell D, Kelso E J, Argent C C, Lee G R, Allen A R, McDermott B J. Temporal characteristics of cardiomyocyte hypertrophy in the spontaneously hypertensive rat. Cardiovasc Pathol 2004; 13:71-8.

[16] Anversa P, Kajstura J, Rota M, Leri A. Regenerating new heart with stem cells. J Clin Invest 2013; 123:62-70.

[17] Hassan M I, Saxena A, Ahmad F. Structure and function of von Willebrand factor. Blood Coagul Fibrinolysis 2012; 23:11-22.
[18] Endl E, Gerdes J. The Ki-67 protein: fascinating forms and an unknown function. Exp Cell Res 2000; 257:231-7.
[19] Boengler K, Schulz R, Heusch G. Connexin 43 signalling and cardioprotection. Heart 2006; 92:1724-7.
[20] Salameh A, Krautblatter S, Karl S, Blanke K, Gomez D R, Dhein S, et al. The signal transduction cascade regulating the expression of the gap junction protein connexin43 by beta-adrenoceptors. Br J Pharmacol 2009; 158:198-208.
[21] Severs N J, Bruce A F, Dupont E, Rothery S. Remodelling of gap junctions and connexin expression in diseased myocardium. Cardiovasc Res 2008; 80:9-19.
[22] Zimmermann W H, Melnychenko I, Eschenhagen T. Engineered heart tissue for regeneration of diseased hearts. Biomaterials 2004; 25:1639-47.

What is claimed is:

1. A method for fabricating a three-dimensional artificial cardiac patch construct comprising:
    coating a substrate with an organic polymer;
    allowing the organic polymer coating to air dry;
    mounting anchors on the organic polymer coating, wherein the anchors are secured to the substrate, and wherein the anchors are utilized to define outer perimeters of the three-dimensional cardiac patch;
    sterilizing the organic polymer coating and the anchors;
    forming a biodegradable gel-based support scaffold on top of the organic polymer coating;
    seeding the biological support scaffold with neonatal cardiac cells;
    culturing the neonatal cardiac cells in vitro to form a real cardiac layer, wherein the culture conditions are suitable for the cells to self-organize to form the real cardiac layer; and
    trimming the real cardiac layer around the outer perimeters defined by the anchors, wherein the real cardiac layer detaches from the substrate to form the three-dimensional cardiac patch.

2. The method of claim 1, wherein the organic polymer is a silicone elastomer.

3. The method of claim 2, wherein the silicone elastomer is polydimethylsiloxane elastomer (PDMS).

4. The method of claim 1, wherein the biodegradable gel-based support scaffold is biocompatible and non-immunogenic.

5. The method of claim 1, wherein the biodegradable gel-based support scaffold is fibrin.

6. The method of claim 5, wherein the fibrin is formed by mixing thrombin and fibrinogen solutions.

7. The method of claim 1, wherein the seeding of the biodegradable gel-based support scaffold comprises layering the neonatal cardiac cells onto the scaffold.

8. The method of claim 1, wherein the seeding of the biodegradable gel-based support scaffold comprises embedding the neonatal cardiac cells into the biodegradable gel-based support scaffold.

9. The method of claim 1, wherein the neonatal cardiac cells comprise fibroblasts, cardiomyocytes, endothelial cells, smooth muscle cells and cardiac stem cells.

10. The method of claim 1, wherein the neonatal cardiac cells are diluted in culture media prior to seeding on the biodegradable gel-based support scaffold.

11. The method of claim 1, wherein the real cardiac layer comprises the neonatal cardiac cells and naturally produced extracellular matrix on top of the biological support scaffold.

12. The method of claim 1, wherein the thickness of the real cardiac layer increases with the density of the neonatal cardiac cells initially seeded.

13. The method of claim 1, wherein the fabricated artificial three-dimensional patch is spontaneously contractile.

14. The method of claim 13, wherein the rate of spontaneous contraction increases with the density of the neonatal cardiac cells initially seeded.

15. The method of claim 1, wherein the fabricated artificial three-dimensional patch exhibits contractile twitch force.

16. The method of claim 15, wherein the contractile twitch force increases with the density of the neonatal cardiac cells initially seeded.

17. The method of claim 1, wherein the artificial three-dimensional patch exhibits angiogenic bud formation.

18. The method of claim 1, wherein the artificial three-dimensional patch exhibits active cell proliferation.

19. The method of claim 1, wherein the artificial three-dimensional patch fabricated is utilized as an implant.

20. The method of claim 19, wherein the recipient is suffering from a congenital heart disease.

21. The method of claim 20, wherein the congenital heart disease is selected from a group consisting of hypoplastic left heart syndrome, tetralogy of fallot, ventricular septal defects, atrial septal defects, endocardial cushion defect.

22. The method of claim 19, wherein the recipient is suffering from a cardiac tissue injury.

23. The method of claim 22, wherein the cardiac tissue injury is due to acute or chronic stress, atheromatous disorders of blood vessels, ischemia, myocardial infarction, inflammatory disease and cardiomyopathies or myocarditis.

24. The method of claim 1, wherein cell adhesion molecules are not utilized.

25. The method of claim 1, wherein an average contraction rate of the three-dimensional cardiac patch is in a range for a normal adult.

26. The method of claim 1, wherein contractile forces of the three-dimensional cardiac patch are in the range of 500-2000 μN.

* * * * *

UNITED STATES PATENT AND TRADEMARK OFFICE
CERTIFICATE OF CORRECTION

PATENT NO. : 10,106,776 B2  
APPLICATION NO. : 14/270766  
DATED : October 23, 2018  
INVENTOR(S) : Ravi K. Birla Page 1 of 1

It is certified that error appears in the above-identified patent and that said Letters Patent is hereby corrected as shown below:

In the Specification

Please replace Column 1, Lines 16-19 with the following text:
--This invention was made with government support under grant number R01 EB011516 awarded by the National Institutes of Health. The government has certain rights in the invention--

Signed and Sealed this  
Twenty-first Day of October, 2025

John A. Squires  
*Director of the United States Patent and Trademark Office*